United States Patent
Salahieh et al.

(10) Patent No.: US 8,840,601 B2
(45) Date of Patent: Sep. 23, 2014

(54) INTRAVASCULAR TISSUE DISRUPTION

(75) Inventors: Amr Salahieh, Saratoga, CA (US); Alan Schaer, San Jose, CA (US); Jeff Krolik, Campbell, CA (US); John Spiridigliozzi, San Mateo, CA (US); Suresh Pai, Mountain View, CA (US); Tom Saul, El Granada, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 313 days.

(21) Appl. No.: 13/071,436

(22) Filed: Mar. 24, 2011

(65) Prior Publication Data

US 2011/0257622 A1  Oct. 20, 2011

Related U.S. Application Data

(60) Provisional application No. 61/317,231, filed on Mar. 24, 2010, provisional application No. 61/324,461, filed on Apr. 15, 2010.

(51) Int. Cl.
| | |
|---|---|
| *A61M 31/00* | (2006.01) |
| *A61M 29/00* | (2006.01) |
| *A61M 1/00* | (2006.01) |
| *A61M 5/00* | (2006.01) |
| *A61M 25/00* | (2006.01) |
| *A61M 25/10* | (2013.01) |
| *A61M 25/04* | (2006.01) |
| *A61M 25/06* | (2006.01) |

(52) U.S. Cl.
CPC ....... *A61M 25/0068* (2013.01); *A61M 25/0054* (2013.01); *A61M 25/1002* (2013.01); *A61M 2025/0096* (2013.01); *A61M 25/0082* (2013.01); *A61M 25/0075* (2013.01); *A61M 25/0074* (2013.01); *A61M 25/04* (2013.01); *A61M 2025/0681* (2013.01); *A61M 25/008* (2013.01); *A61M 2025/0079* (2013.01); *A61M 2025/1097* (2013.01); *A61M 25/0097* (2013.01)
USPC ........... 604/500; 604/509; 604/105; 604/118; 604/246

(58) Field of Classification Search
USPC ......... 604/604, 500, 507, 508, 509, 104–109, 604/164.02, 523, 246, 236
See application file for complete search history.

(56) References Cited

U.S. PATENT DOCUMENTS

| | | |
|---|---|---|
| 4,547,193 A | 10/1985 | Rydell |
| 4,634,432 A | 1/1987 | Kocak |

(Continued)

FOREIGN PATENT DOCUMENTS

| | | |
|---|---|---|
| DE | 4104092 A1 | 8/1991 |
| EP | 0637943 B1 | 4/1998 |

(Continued)

OTHER PUBLICATIONS

Salahieh et al.; U.S. Appl. No. 13/106,658 entitled "Low Profile Electrode Assembly ," filed May 12, 2011.

(Continued)

*Primary Examiner* — Kevin C Sirmons
*Assistant Examiner* — William Carpenter
(74) *Attorney, Agent, or Firm* — Shay Glenn LLP

(57) ABSTRACT

Disrupting tissue and devices and systems for disrupting tissue. The disclosure describes ways to deliver moieties to a target tissue, where the target tissue in general is not at the point of introduction, in such a way that minimal damage is produced in the tissue at the point of introduction. In some embodiments this is accomplished by jetting fluid at high velocity into the target tissue. The disclosure further describes novel agents deliverable in such systems for use in remodeling tissues. Some of these agents comprise a liquid while others do not. Additionally, although not specifically described in detail much of the disclosure may additionally be used in the delivery of therapeutic drugs.

4 Claims, 15 Drawing Sheets

(56) References Cited

U.S. PATENT DOCUMENTS

| | | | |
|---|---|---|---|
| 4,692,139 A | 9/1987 | Stiles | |
| 4,726,382 A | 2/1988 | Boehmer et al. | |
| 4,890,623 A | 1/1990 | Cook et al. | |
| 4,968,306 A * | 11/1990 | Huss et al. | 604/264 |
| 5,010,895 A | 4/1991 | Maurer et al. | |
| 5,041,089 A | 8/1991 | Mueller et al. | |
| 5,069,674 A | 12/1991 | Fearnot et al. | |
| 5,180,376 A | 1/1993 | Fischell | |
| 5,209,741 A | 5/1993 | Spaeth | |
| 5,213,576 A * | 5/1993 | Abiuso et al. | 604/103.01 |
| 5,228,442 A | 7/1993 | Imran | |
| 5,306,250 A * | 4/1994 | March et al. | 604/104 |
| 5,309,910 A | 5/1994 | Edwards et al. | |
| 5,311,866 A | 5/1994 | Kagan et al. | |
| 5,343,860 A | 9/1994 | Metzger et al. | |
| 5,391,200 A | 2/1995 | KenKnight et al. | |
| 5,443,470 A | 8/1995 | Stern et al. | |
| 5,496,267 A * | 3/1996 | Drasler et al. | 604/22 |
| 5,505,730 A | 4/1996 | Edwards | |
| 5,515,848 A | 5/1996 | Corbett, III et al. | |
| 5,524,338 A | 6/1996 | Martyniuk et al. | |
| 5,531,679 A * | 7/1996 | Schulman et al. | 604/65 |
| 5,540,679 A | 7/1996 | Fram et al. | |
| 5,558,672 A | 9/1996 | Edwards et al. | |
| 5,562,720 A | 10/1996 | Stern et al. | |
| 5,569,241 A | 10/1996 | Edwards | |
| 5,571,086 A * | 11/1996 | Kaplan et al. | 604/96.01 |
| 5,571,088 A | 11/1996 | Lennox et al. | |
| 5,573,520 A | 11/1996 | Schwartz et al. | |
| 5,575,772 A | 11/1996 | Lennox | |
| 5,575,788 A | 11/1996 | Baker et al. | |
| 5,609,574 A * | 3/1997 | Kaplan et al. | 604/508 |
| 5,609,606 A | 3/1997 | O'Boyle | |
| 5,626,564 A * | 5/1997 | Zhan et al. | 604/164.01 |
| 5,630,837 A | 5/1997 | Crowley | |
| 5,681,308 A | 10/1997 | Edwards et al. | |
| 5,713,860 A * | 2/1998 | Kaplan et al. | 604/103.01 |
| 5,715,825 A | 2/1998 | Crowley | |
| 5,718,701 A | 2/1998 | Shai et al. | |
| 5,735,846 A | 4/1998 | Panescu et al. | |
| 5,769,846 A | 6/1998 | Edwards et al. | |
| 5,779,698 A | 7/1998 | Clayman et al. | |
| 5,792,118 A | 8/1998 | Kurth et al. | |
| 5,800,408 A * | 9/1998 | Strauss et al. | 604/264 |
| 5,836,874 A | 11/1998 | Swanson et al. | |
| 5,846,196 A | 12/1998 | Siekmeyer et al. | |
| 5,846,238 A | 12/1998 | Jackson et al. | |
| 5,846,239 A | 12/1998 | Swanson et al. | |
| 5,853,411 A | 12/1998 | Whayne et al. | |
| 5,860,974 A | 1/1999 | Abele | |
| 5,871,483 A | 2/1999 | Jackson et al. | |
| 5,879,348 A | 3/1999 | Owens et al. | |
| 5,882,332 A | 3/1999 | Wijay | |
| 5,888,577 A | 3/1999 | Griffin, III et al. | |
| 5,904,651 A | 5/1999 | Swanson et al. | |
| 5,938,660 A | 8/1999 | Swartz et al. | |
| 5,961,513 A | 10/1999 | Swanson et al. | |
| 5,991,650 A | 11/1999 | Swanson et al. | |
| 6,004,269 A | 12/1999 | Crowley et al. | |
| 6,012,457 A | 1/2000 | Lesh | |
| 6,024,740 A | 2/2000 | Lesh et al. | |
| 6,052,607 A | 4/2000 | Edwards et al. | |
| 6,123,718 A | 9/2000 | Tu et al. | |
| 6,142,993 A | 11/2000 | Whayne et al. | |
| 6,163,726 A | 12/2000 | Wolf | |
| 6,164,283 A | 12/2000 | Lesh | |
| 6,206,912 B1 | 3/2001 | Goldsteen et al. | |
| 6,292,689 B1 | 9/2001 | Wallace et al. | |
| 6,402,746 B1 | 6/2002 | Whayne et al. | |
| 6,460,545 B2 | 10/2002 | Kordis | |
| 6,471,683 B2 * | 10/2002 | Drasler et al. | 604/508 |
| 6,500,174 B1 | 12/2002 | Maguire et al. | |
| 6,514,249 B1 | 2/2003 | Maguire et al. | |
| 6,558,378 B2 | 5/2003 | Sherman et al. | |
| 6,572,609 B1 | 6/2003 | Farr et al. | |
| 6,572,612 B2 | 6/2003 | Stewart et al. | |
| 6,595,989 B1 | 7/2003 | Schaer | |
| 6,635,027 B1 * | 10/2003 | Cragg et al. | 604/22 |
| 6,635,054 B2 | 10/2003 | Fjield et al. | |
| 6,641,553 B1 | 11/2003 | Chee et al. | |
| 6,652,515 B1 | 11/2003 | Maguire et al. | |
| 6,660,002 B1 | 12/2003 | Edwards et al. | |
| 6,736,811 B2 | 5/2004 | Panescu et al. | |
| 6,743,226 B2 | 6/2004 | Cosman et al. | |
| 6,771,996 B2 | 8/2004 | Bowe et al. | |
| 6,780,183 B2 | 8/2004 | Jimenez, Jr. et al. | |
| 6,808,524 B2 | 10/2004 | Lopath et al. | |
| 6,814,730 B2 | 11/2004 | Li | |
| 6,869,431 B2 | 3/2005 | Maguire et al. | |
| 6,872,183 B2 | 3/2005 | Sampson et al. | |
| 6,872,206 B2 | 3/2005 | Edwards et al. | |
| 6,911,027 B1 | 6/2005 | Edwards et al. | |
| 6,942,657 B2 | 9/2005 | Sinofsky et al. | |
| 6,964,649 B2 | 11/2005 | Goll | |
| 6,978,174 B2 | 12/2005 | Gelfand et al. | |
| 7,004,923 B2 * | 2/2006 | Deniega et al. | 604/4.01 |
| 7,048,733 B2 | 5/2006 | Hartley et al. | |
| 7,115,122 B1 | 10/2006 | Swanson et al. | |
| 7,137,395 B2 | 11/2006 | Fried et al. | |
| 7,150,745 B2 | 12/2006 | Stern et al. | |
| 7,162,303 B2 | 1/2007 | Levin et al. | |
| 7,207,984 B2 | 4/2007 | Farr et al. | |
| 7,220,269 B1 * | 5/2007 | Ansel et al. | 606/159 |
| 7,226,448 B2 | 6/2007 | Bertolero et al. | |
| 7,232,437 B2 | 6/2007 | Berman et al. | |
| 7,238,179 B2 | 7/2007 | Brucker et al. | |
| 7,238,180 B2 | 7/2007 | Mester et al. | |
| 7,267,674 B2 | 9/2007 | Brucker et al. | |
| 7,286,866 B2 | 10/2007 | Okerlund et al. | |
| 7,291,146 B2 | 11/2007 | Steinke et al. | |
| 7,310,150 B2 | 12/2007 | Guillermo et al. | |
| 7,320,677 B2 | 1/2008 | Brouillette | |
| 7,346,381 B2 | 3/2008 | Okerlund et al. | |
| 7,357,796 B2 | 4/2008 | Farr et al. | |
| 7,365,859 B2 | 4/2008 | Yun et al. | |
| 7,366,376 B2 | 4/2008 | Shishkov et al. | |
| 7,371,231 B2 | 5/2008 | Rioux et al. | |
| 7,382,949 B2 | 6/2008 | Bouma et al. | |
| 7,396,355 B2 | 7/2008 | Goldman et al. | |
| 7,406,970 B2 | 8/2008 | Zikorus et al. | |
| 7,413,568 B2 | 8/2008 | Swanson et al. | |
| 7,418,169 B2 | 8/2008 | Tearney et al. | |
| 7,429,260 B2 | 9/2008 | Underwood et al. | |
| 7,429,261 B2 | 9/2008 | Kunis et al. | |
| 7,445,618 B2 | 11/2008 | Eggers et al. | |
| 7,447,408 B2 | 11/2008 | Bouma et al. | |
| 7,452,358 B2 | 11/2008 | Stern et al. | |
| 7,468,062 B2 | 12/2008 | Oral et al. | |
| 7,473,251 B2 | 1/2009 | Knowlton et al. | |
| 7,481,808 B2 | 1/2009 | Koyfman et al. | |
| 7,481,809 B2 | 1/2009 | Stern et al. | |
| 7,489,969 B2 | 2/2009 | Knudson et al. | |
| 7,507,236 B2 | 3/2009 | Eggers et al. | |
| 7,510,555 B2 | 3/2009 | Kanzius | |
| 7,519,096 B2 | 4/2009 | Bouma et al. | |
| 7,529,393 B2 | 5/2009 | Peszynski et al. | |
| 7,538,859 B2 | 5/2009 | Tearney et al. | |
| 7,617,005 B2 | 11/2009 | Demarais et al. | |
| 7,620,451 B2 | 11/2009 | Demarais et al. | |
| 7,653,438 B2 | 1/2010 | Deem et al. | |
| 7,669,309 B2 | 3/2010 | Johnson et al. | |
| 7,756,583 B2 | 7/2010 | Demarais et al. | |
| 7,853,333 B2 | 12/2010 | Demarais | |
| 7,937,143 B2 | 5/2011 | Demarais et al. | |
| 2002/0002384 A1 | 1/2002 | Gilson et al. | |
| 2002/0095147 A1 | 7/2002 | Shadduck | |
| 2003/0097121 A1 * | 5/2003 | Jolly et al. | 604/891.1 |
| 2003/0236443 A1 | 12/2003 | Cespedes et al. | |
| 2006/0041277 A1 | 2/2006 | Deem et al. | |
| 2006/0100618 A1 | 5/2006 | Chan et al. | |
| 2006/0206150 A1 | 9/2006 | Demarais et al. | |
| 2006/0212076 A1 | 9/2006 | Demarais et al. | |
| 2006/0212078 A1 | 9/2006 | Demarais et al. | |
| 2006/0247701 A1 | 11/2006 | Zacouto | |

(56) References Cited

U.S. PATENT DOCUMENTS

| | | |
|---|---|---|
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0060888 A1* | 3/2007 | Goff et al. ............... 604/118 |
| 2007/0078507 A1 | 4/2007 | Zacouto |
| 2007/0112422 A1 | 5/2007 | Dehdashtian |
| 2007/0118094 A1 | 5/2007 | Bingham et al. |
| 2007/0129760 A1 | 6/2007 | Demarais et al. |
| 2007/0135875 A1 | 6/2007 | Demarais et al. |
| 2007/0213671 A1* | 9/2007 | Hiatt .................. 604/164.01 |
| 2007/0225634 A1 | 9/2007 | Ferren et al. |
| 2007/0244501 A1 | 10/2007 | Horn et al. |
| 2008/0188912 A1 | 8/2008 | Stone et al. |
| 2008/0205481 A1* | 8/2008 | Faries et al. ............... 374/138 |
| 2008/0275445 A1 | 11/2008 | Kelly et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0227885 A1 | 9/2009 | Lowery et al. |
| 2009/0240249 A1 | 9/2009 | Chan et al. |
| 2009/0254142 A1 | 10/2009 | Edwards et al. |
| 2009/0312696 A1 | 12/2009 | Copa et al. |
| 2009/0312754 A1 | 12/2009 | Lenihan et al. |
| 2010/0204560 A1 | 8/2010 | Salahieh et al. |
| 2010/0331776 A1 | 12/2010 | Salahieh et al. |
| 2011/0046600 A1 | 2/2011 | Crank |
| 2011/0077579 A1* | 3/2011 | Harrison et al. ............ 604/20 |
| 2011/0104060 A1 | 5/2011 | Seward |
| 2011/0104061 A1 | 5/2011 | Seward |
| 2013/0138082 A1 | 5/2013 | Salahieh et al. |

FOREIGN PATENT DOCUMENTS

| | | |
|---|---|---|
| EP | 0723467 B1 | 4/2002 |
| EP | 0693955 B1 | 1/2003 |
| EP | 1382366 A1 | 1/2004 |
| EP | 2335757 A2 | 6/2011 |
| WO | WO 99/00060 A1 | 1/1999 |
| WO | WO 99/48545 A1 | 9/1999 |
| WO | WO 00/66014 A1 | 11/2000 |
| WO | WO2005/025645 A2 | 3/2005 |
| WO | WO2006/078444 A1 | 7/2006 |
| WO | WO 2009/067695 A1 | 5/2009 |
| WO | WO 2009/132137 A1 | 10/2009 |
| WO | WO2010/065133 A2 | 6/2010 |

OTHER PUBLICATIONS

Salahieh et al.; U.S. Appl. No. 13/351,962 entitled "Intravascular Tissue Disruption," filed Jan. 17, 2012.

Drafts, Bill; Acoustic wave technology sensors; Sensors Weekly (Questex Media Group); 10 pgs.; Oct. 1, 2000 (http://www.sensorsmag.com/sensors/acoustic-ultrasound/acoustic-wave-technology-sensors-936).

Salahieh et al.; U.S. Appl. No. 13/830,624 entitled "Local Sympathectomy for PVD," filed Mar. 14, 2013.

Salahieh et al.; U.S. Appl. No. 61/622,495 entitled "Energy Delivery Device with Rapid Exchange Features," filed Apr. 10, 2012.

Salahieh et al.; U.S. Appl. No. 61/624,206 entitled "Energy delivery device and methods of use," filed Apr. 13, 2012.

Salahieh et al.; U.S. Appl. No. 13/943,633 entitled "Low Profile Electrode Assembly," filed Jul. 16, 2013.

Salahieh et al.; U.S. Appl. No. 14/023,343 entitled "Steerable Delivery Sheaths," filed Sep. 11, 2013.

* cited by examiner

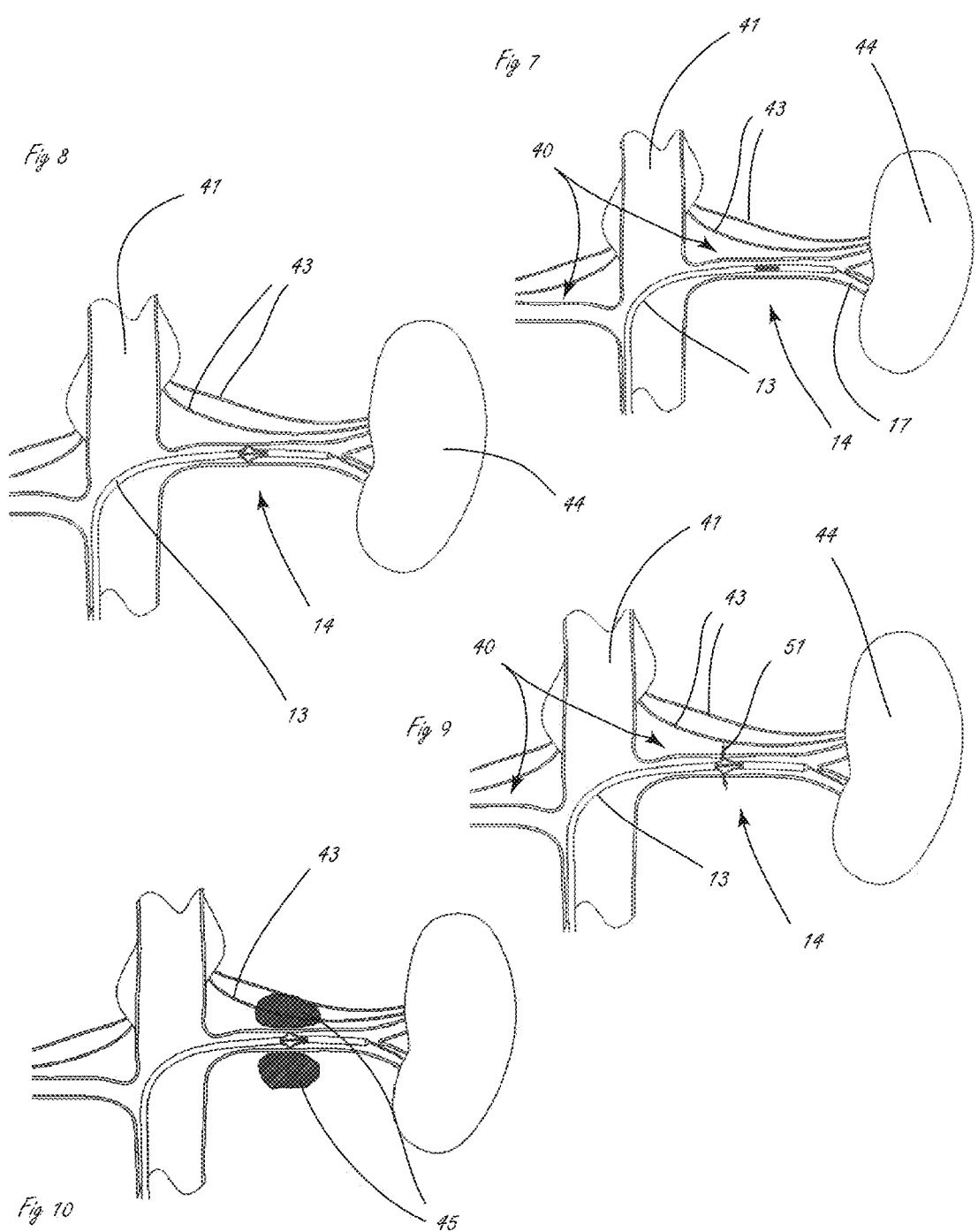

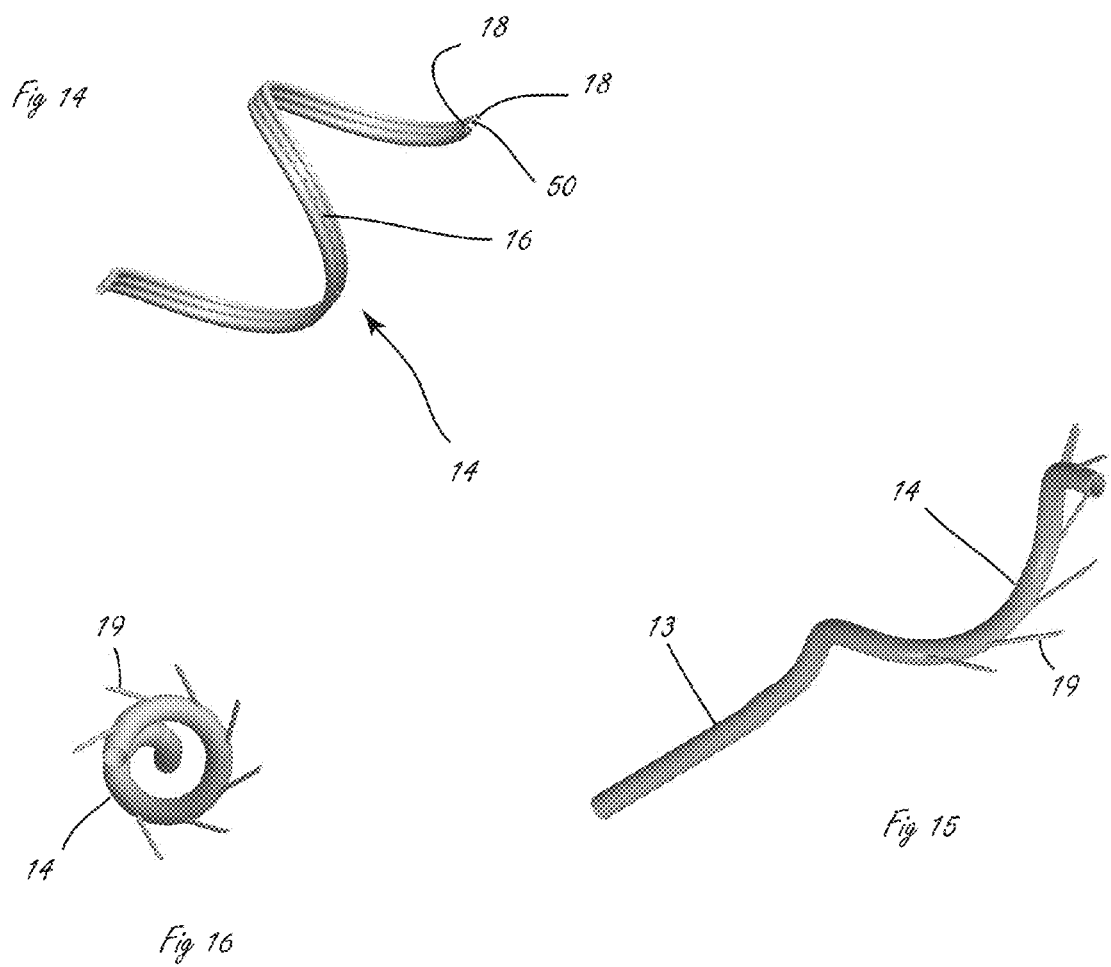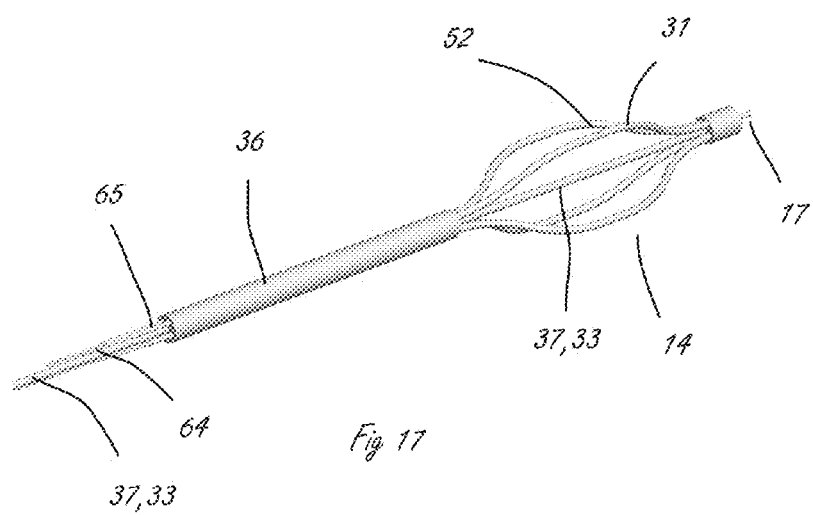

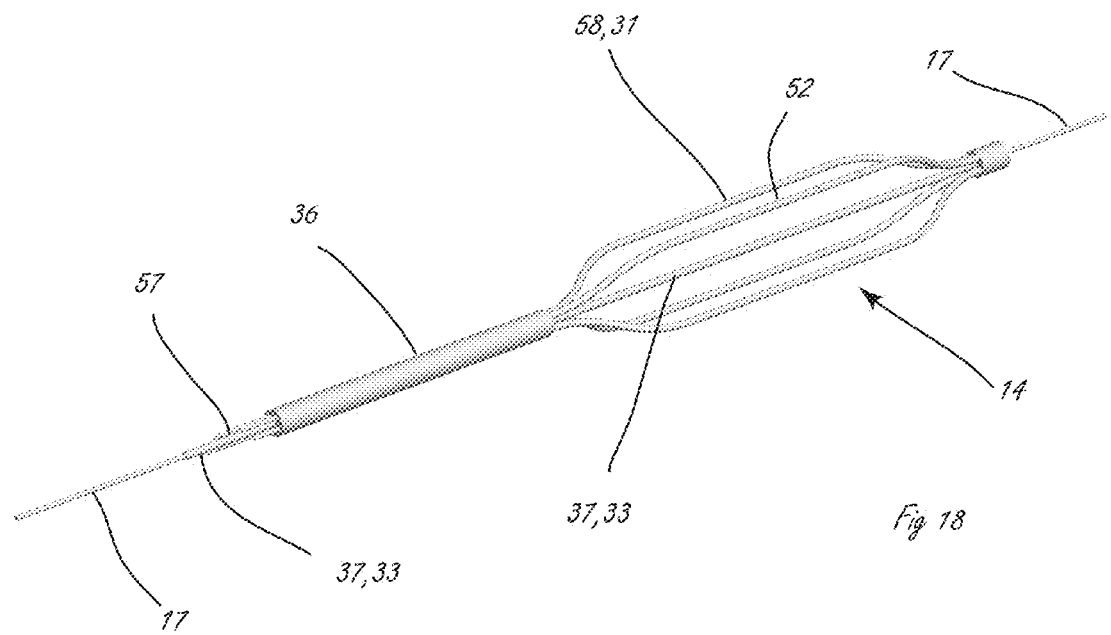
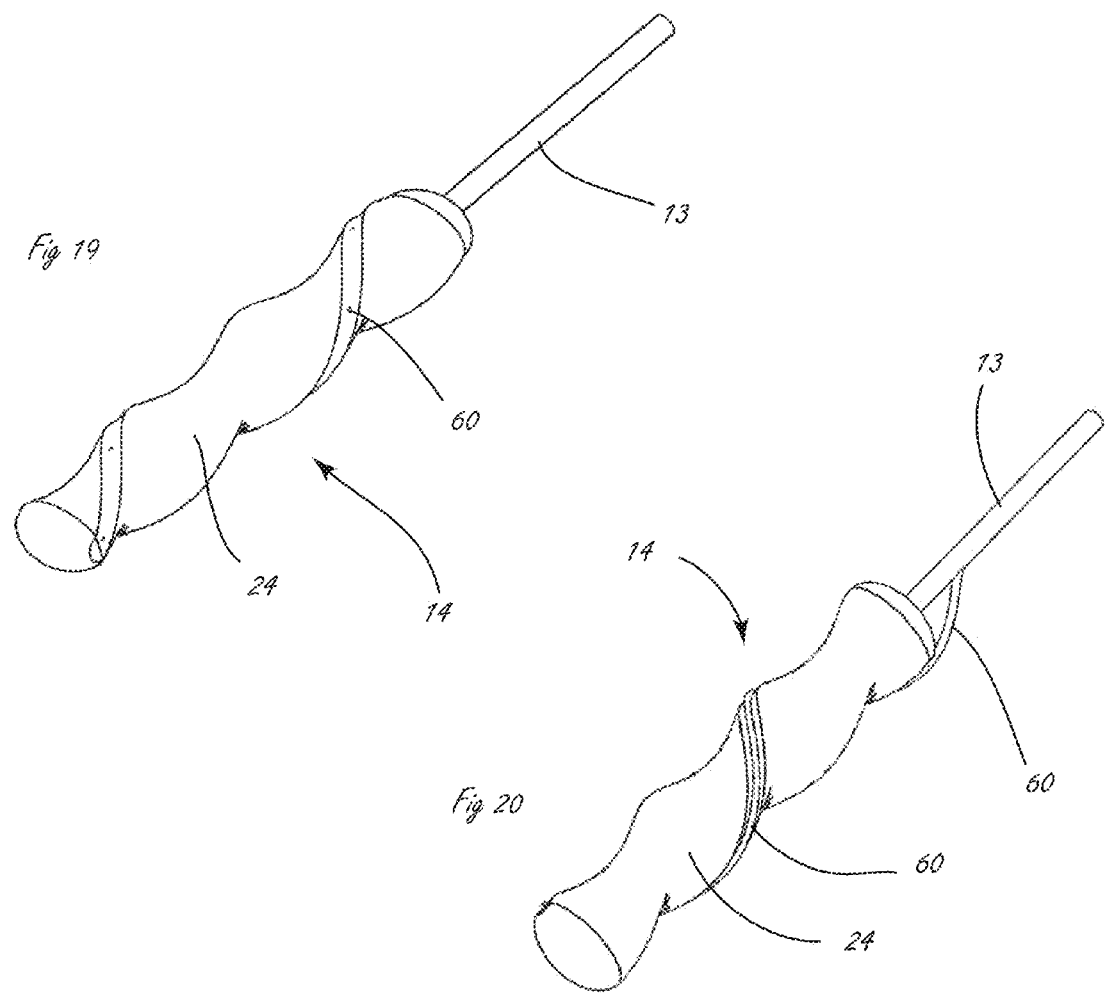

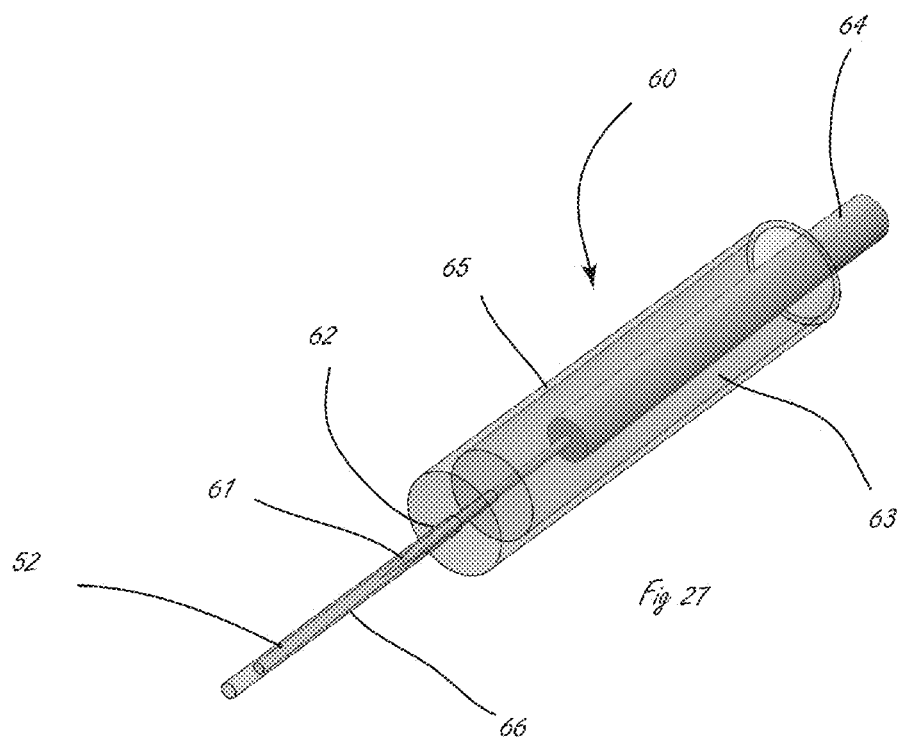
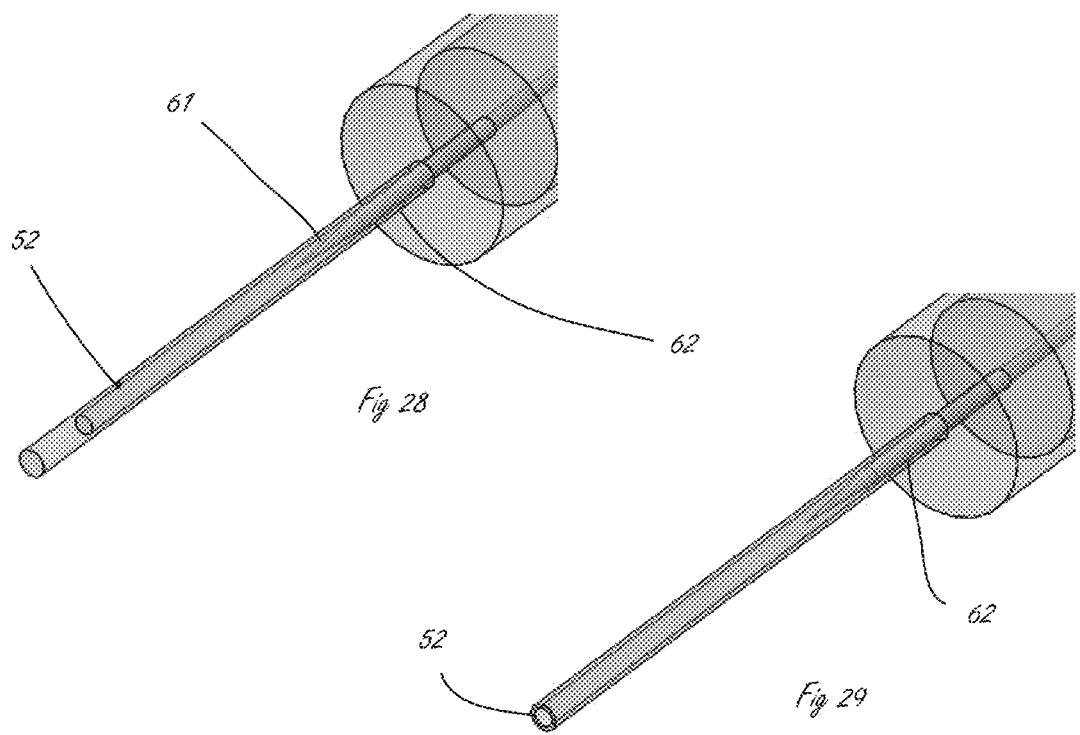

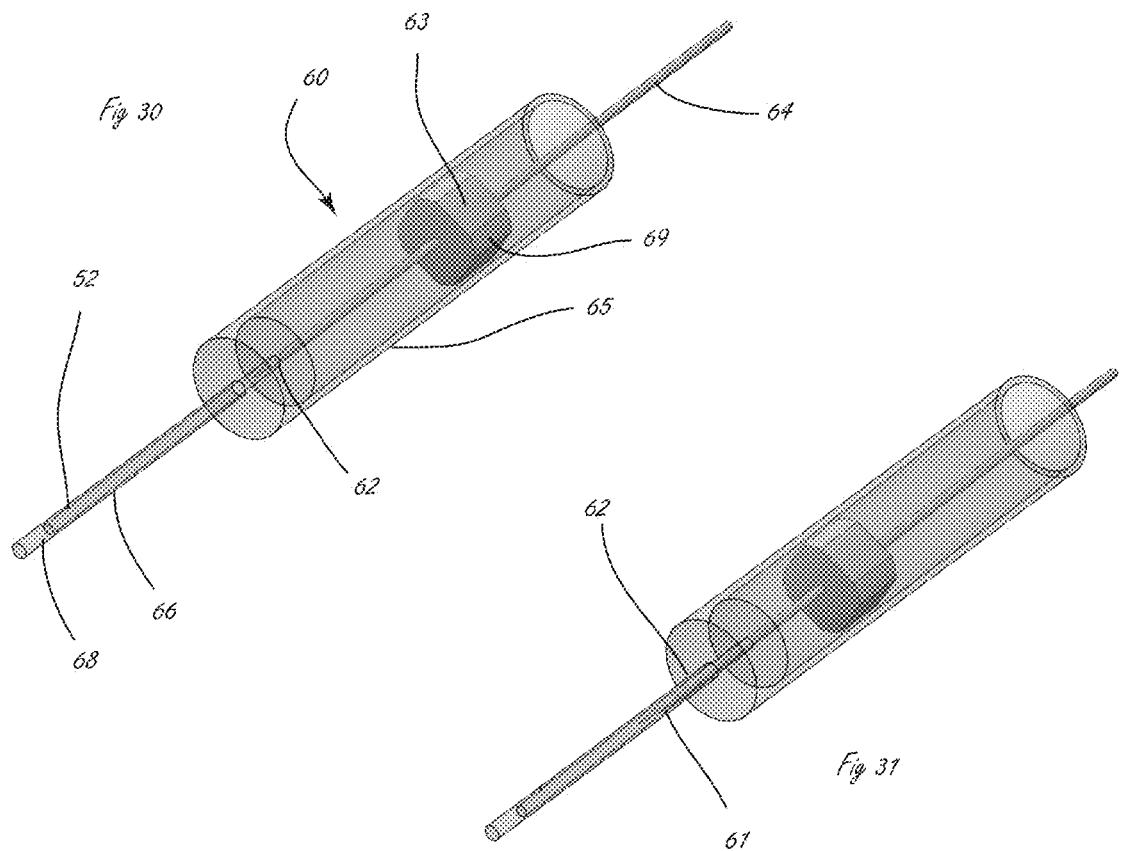
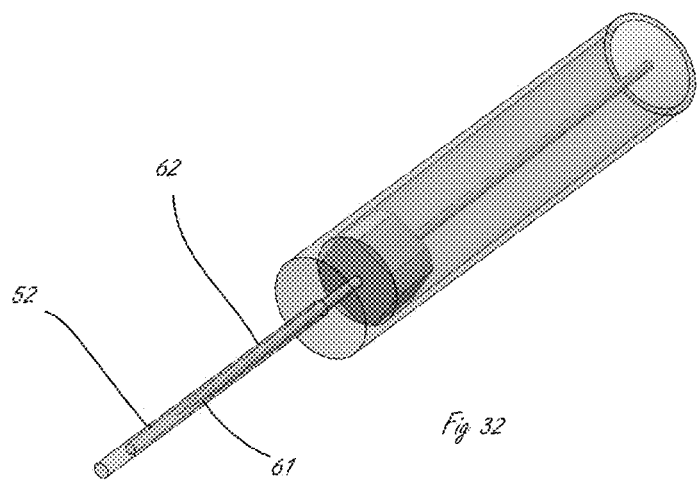

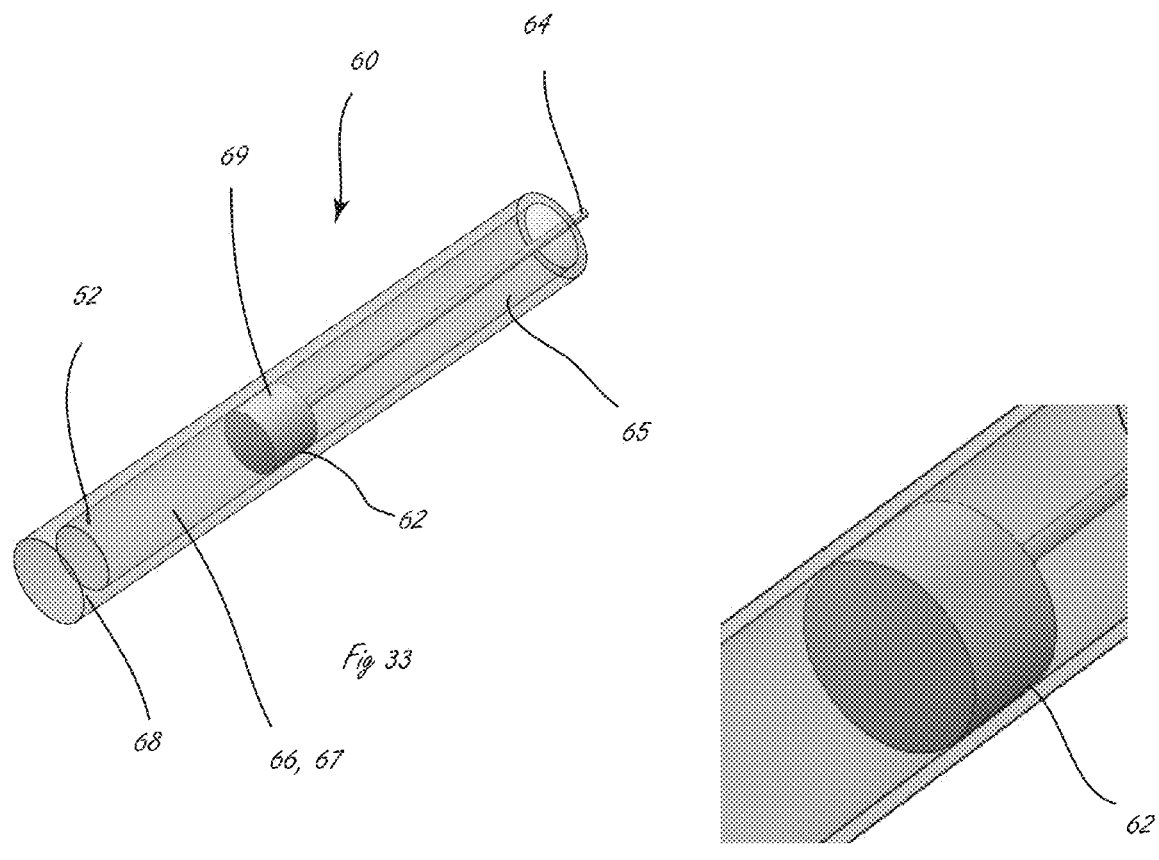
Fig 33
Fig 34
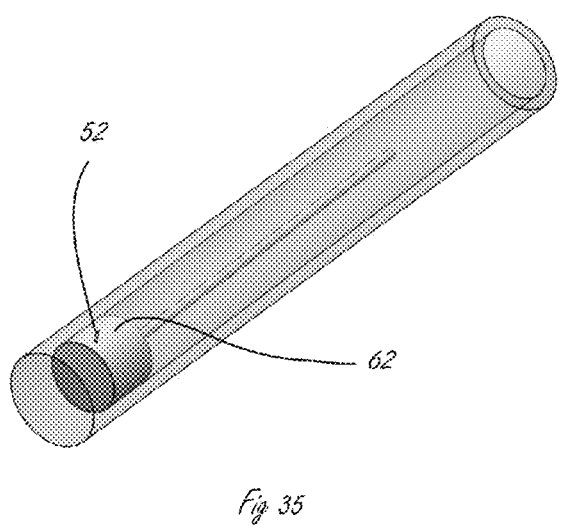
Fig 35

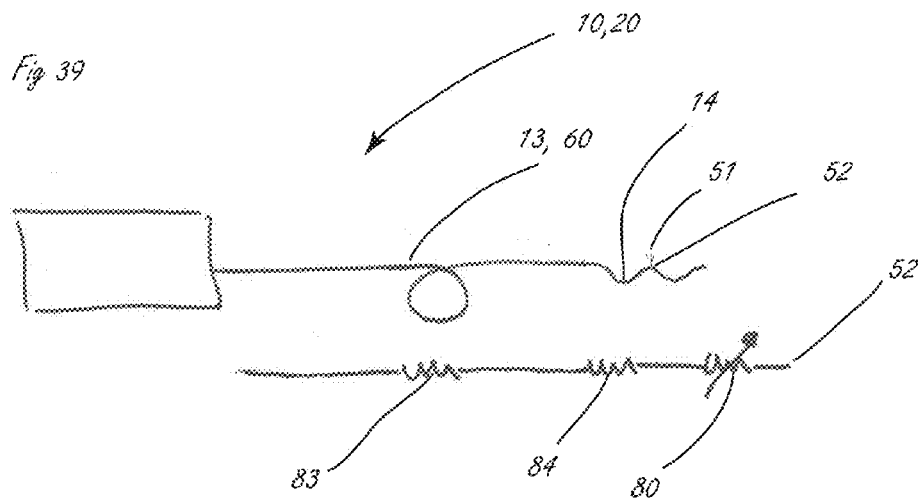
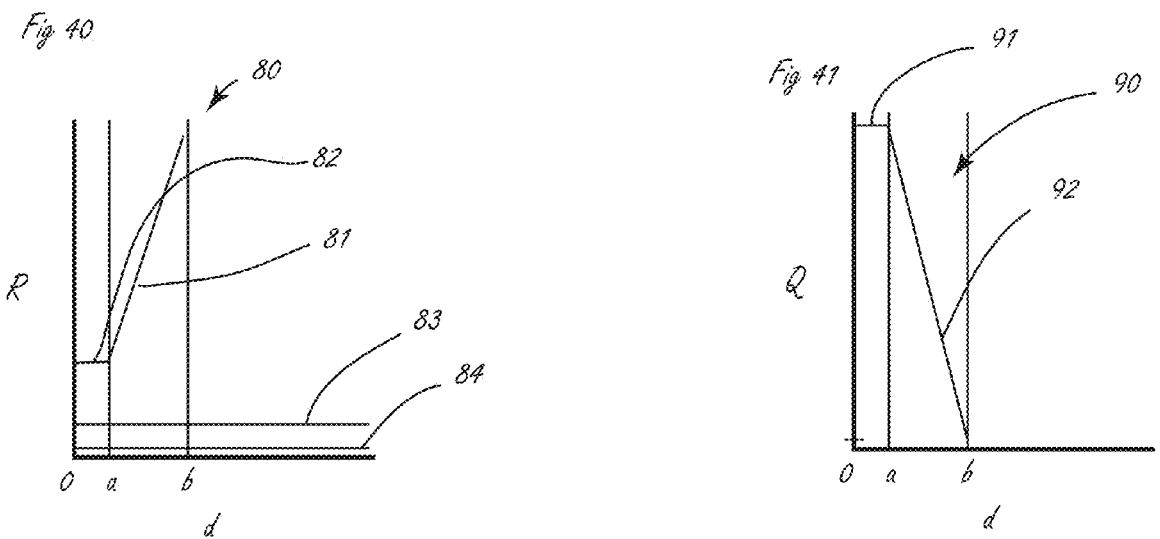
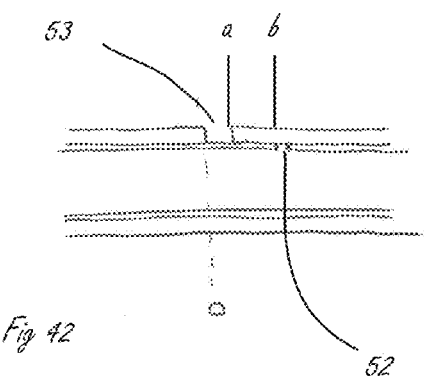

83  84  85

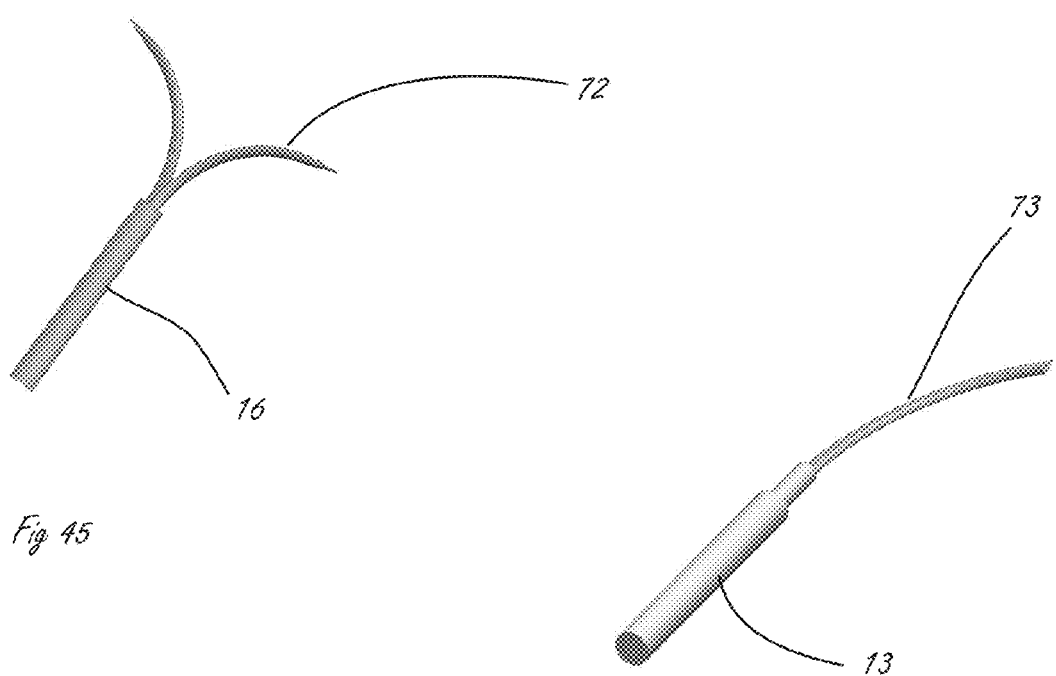
Fig 45
Fig 46
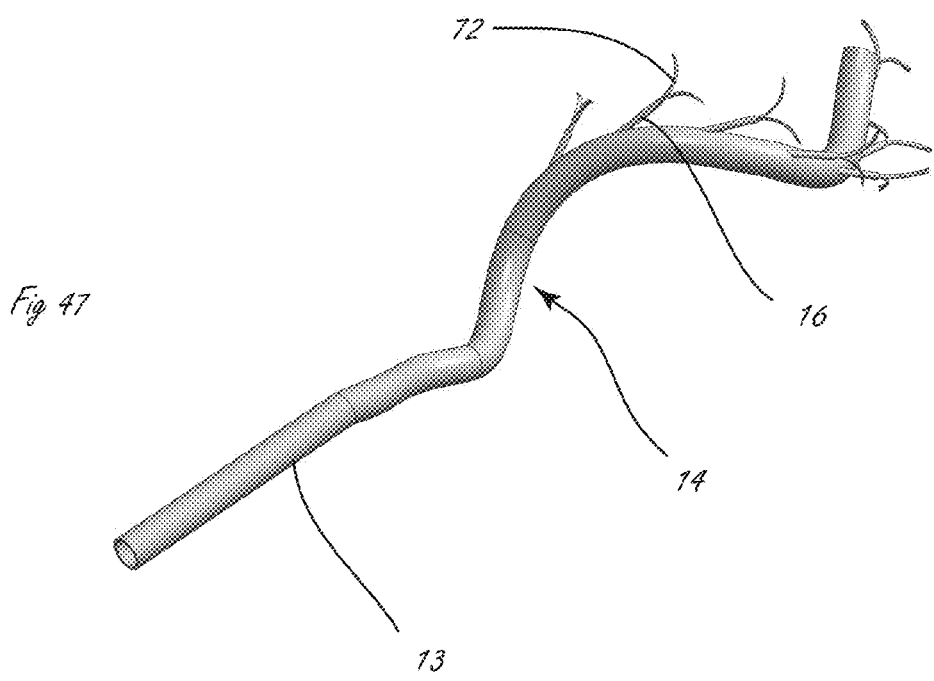
Fig 47

INTRAVASCULAR TISSUE DISRUPTION

CROSS-REFERENCE

This application claims the benefit of U.S. Provisional Application No. 61/317,231, filed Mar. 24, 2010, and U.S. Provisional Application No. 61/324,461, filed Apr. 15, 2010, the disclosures of which are incorporated herein by reference in their entirety.

BACKGROUND OF THE INVENTION

Various treatments to bodily tissue have been attempted. Devices that can deliver a fluid from a distal end port of a catheter have been described. Devices have been described that have a valve at a distal port that allows fluid to flow through the valve in an open configuration and prevents fluid from flowing through the valve in a closed configuration. Devices have also been described that can create microfluidic pulsed jets at the distal end of a catheter. Additionally, intravascular devices that include elements that pierce lumen walls can be deployed within a lumen and deliver medication into a lumen wall. Some devices have a plurality of delivery ports through which fluids are delivered simultaneously. These devices and methods of use have one or more shortcomings for which the disclosure herein compensates.

SUMMARY OF THE INVENTION

One aspect of the disclosure is a method of controlling the delivery of fluid from a medical delivery device, comprising: a medical device comprising a distal delivery region comprising a plurality of fluid controls; and selectively regulating the flow of a fluid through the plurality of fluid controls. In some embodiments selectively regulating comprises allowing the fluid to be delivered from a first fluid control while minimizing the fluid that is delivered from a second fluid control. In some embodiments selectively regulating comprises increasing the flow of fluid from a first fluid control without increasing the flow of fluid through a second fluid control. In some embodiments selectively regulating comprises increasing the fluid flow from a first fluid control a first amount and increasing the flow of fluid from a second fluid control a second amount, wherein the first amount is different than the second amount. In some embodiments selectively regulating comprising moving a first fluid control from a closed configuration to an open configuration without moving a second fluid control from a closed configuration to an open configuration. Moving the first control to the open configuration can comprise moving a first valve element with a first aperture therein relative to a second valve element with a second aperture therein until the apertures are in alignment. Moving the first fluid control to the open configuration can cause the fluid to flow from the first control at a high velocity, while the fluid flows out of the second fluid control at a low velocity. In some embodiments selectively regulating comprises flowing the fluid out of a first fluid control at a high velocity and flowing the fluid out of a second fluid control at a low velocity.

One aspect of the disclosure is a method of regulating the volume of a fluid delivered from a medical device, comprising: a medical device comprising a distal delivery region comprising a fluid control in communication with a fluid source, wherein the fluid control comprises a first control element with a first aperture therein and a second control element with a second aperture therein; positioning the distal delivery region near a target location within a patient; and regulating the volume of fluid released from the fluid control by moving the apertures into alignment to increase the flow of the fluid through the fluid control. In some embodiments the regulating step occurs independently of transience generated at a fluid pressure source. In some embodiments the fluid source is disposed external to the patient, further comprising maintaining a substantially constant pressure at the fluid source. The method can further comprise varying the fluid velocity at the fluid control to regulate the volume of fluid released. In some embodiments regulating the volume of fluid released further comprises moving the apertures out of alignment to decrease the flow of fluid out of the fluid control. In some embodiments the first control element comprises a first tubular member and the second control element comprises a second tubular member disposed within the first tubular member, and wherein moving the apertures into alignment comprises moving the first tubular member relative to the second tubular member to thereby move the first aperture relative to the second aperture. Moving the first tubular member relative to the second tubular member can comprise at least one of axial movement and rotational movement.

One aspect of the disclosure is a method of periluminal tissue damage, comprising positioning a delivery device within a lumen without piercing the lumen wall; delivering a fluid agent from the delivery device through the lumen wall; and damaging tissue peripheral to the lumen wall with the fluid agent. In some embodiments the lumen wall comprises an intimal layer, and wherein the damaging step comprises damaging nerve cells peripheral to the intimal layer of the lumen wall. Damaging can comprise damaging nerves cells while minimally damaging tissue in the intimal layer of the vessel wall. The lumen wall can comprise a medial layer, and wherein damaging comprises damaging tissue within the medial layer. Damaging tissue can comprise damaging cells in at least one of a medial layer of the lumen and nerve cells disposed within the adventitial layer. A damage cross section can increases as the radial distance from the intimal layer increases.

In some embodiments the delivery device comprises a first fluid control and a second fluid control, wherein delivering comprises delivering the fluid agent from the first fluid control to create a first damage region, and delivering the fluid agent from the second fluid control creates a second damage region, wherein portions of the first and second regions overlap. In some embodiments damaging comprises damaging tissue with the direct mechanical interaction of the fluid. In some embodiments damaging is caused by chemical interactions with the fluid, such as a hypotonic, a hypertonic fluid, a fluid that self-heats on interaction with tissue, a fluid that has a pH significantly different from the pH of the tissue, a fluid that comprises material toxic to the tissue, a fluid that comprises material toxic to a particular tissue, a fluid that comprises material which becomes toxic on interaction with the tissue, or a fluid that comprises material which is capable of absorbing energy delivered from a source external to the body.

In some embodiments delivering a fluid agent from the delivery device through the lumen wall comprises delivering the fluid agent towards neural tissue peripheral to an intimal layer of the lumen. In some embodiments damaging comprises damaging renal nerve tissue peripheral to a lumen of a renal artery. In some embodiments damaging renal nerve tissue reduces hypertension.

One aspect of the disclosure is an apparatus for releasing fluid within a patient's body, comprising: an elongate member comprising a distal region comprising a plurality of fluid controls, a lumen extending through the distal region and in fluid communication with the plurality of fluid controls, wherein the lumen is adapted to be in fluid communication with a fluid source, wherein each of the plurality of fluid controls is adapted to be selectively addressable to regulate the volume of a fluid that is released from the lumen and out the plurality of fluid controls.

In some embodiments the fluid control has a closed configuration and an open configuration, wherein in the closed configuration a substantially smaller volume of fluid, such as no fluid, is allowed to be released out of the fluid control than in the open configuration. In the open configuration the fluid control can be adapted to release the fluid at high velocity. In some embodiments the distal region comprises a plurality of fluid controls in fluid communication with the lumen, each fluid control has open and closed configurations, and wherein each fluid control is adapted to regulate the volume of fluid that is released from the fluid control when the fluid is delivered at high velocity. The plurality of fluid controls can be adapted to be individually opened. In some embodiments the fluid control is adapted to be in fluid communication with a fluid source maintained at a substantially constant pressure. The fluid control can control the volume of fluid that is released from the fluid control while the fluid source is maintained at the substantially constant pressure.

One aspect of the disclosure is an apparatus for controllably releasing fluid within a patient's body, comprising: a first tubular element with a first aperture therein; a second tubular element with a second aperture therein, wherein the second tubular element is disposed within the first tubular element and movable relative to the first tubular element, wherein the second tubular element has a lumen therethrough adapted to be in fluid communication with a fluid source, and wherein the apertures have an aligned configuration that allows a fluid to pass from the lumen through the first and second apertures. In some embodiments the apertures have an aligned configuration that allows a fluid to pass through the apertures at a high velocity. In some embodiments the second aperture has a smaller maximum dimension than a maximum dimension of the first aperture. In some embodiments the apparatus further comprises a fluid source maintained at substantially a constant pressure. The apertures can be adapted to release a fluid therethrough at high velocity. The apertures can have an aligned configuration that allows fluid to pass therethrough when the fluid source is maintained at a substantially constant first pressure during a first delivery cycle and when the fluid source is maintained at a substantially constant second pressure during a second delivery cycle, wherein the first and second pressure are different. In some embodiments the first tubular element has a deformed treatment configuration wherein at least a portion of the first tubular element is adapted to engage a lumen wall in which it is positioned. The deformed treatment configuration can be substantially spiral-shaped. The apparatus can further comprise an expandable element that is adapted to deform the first tubular element into contact with the lumen wall. The expandable element can comprise a balloon. The expandable element can be moveable relative to the first tubular element to cause the first tubular element to be deformed into the treatment configuration. In some embodiments the apparatus further comprises a piercing element in fluid communication with the first aperture and extending from the first aperture, wherein the piercing element is adapted to pierce tissue and allow for the fluid to flow from the aperture and out of the piercing element. In some embodiments the apertures have a non-aligned configuration that is adapted to allow fluid to flow therethrough at a low velocity.

One aspect of the disclosure is an apparatus for controllably releasing fluid within a patient's body, comprising: an elongate member comprising a distal end, a proximal end, and a therapy portion in between the ends; the therapy portion comprises a plurality of expandable elongate elements, each with a delivery configuration and a treatment configuration, wherein each of the plurality of expandable elongate elements comprises a fluid control, and in the delivery configuration the control faces a first direction and in the treatment configuration the control faces a second direction different than first direction. In some embodiments the second direction is generally orthogonal to a longitudinal axis of the elongate member. In some embodiments the first direction is substantially parallel to a longitudinal axis of the elongate member. In some embodiments the expandable elongate elements are tubular elements, and wherein the fluid controls are provided by removing sections from the tubular elements. In some embodiments the fluid controls are proximal to distal ends of the elongate elements. In some embodiments the expandable elongate elements are adapted to preferentially bend in the region of the fluid ports in the treatment configurations. In some embodiments the expandable elongate elements are self-expanding. In some embodiments the expandable elongate elements are actuatable.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIGS. 7-10 illustrate an exemplary method of remodeling renal nerves surrounding a renal artery.

FIG. 14 illustrates an exemplary portion of a distal delivery region, wherein a spiral element comprises two spring elements on either side of a valve.

FIGS. 15 and 16 illustrate perspective and end views, respectively, of an exemplary embodiment of the distal delivery region that includes a tubular element, and includes a plurality of penetrating remodeling elements.

FIGS. 17 and 18 illustrate exemplary embodiments of distal delivery region including a plurality of expandable tubular elements.

FIGS. 19 and 20 illustrate exemplary distal delivery regions incorporating expandable balloons.

FIGS. 27-32 illustrate exemplary needle valves that can be activated from a proximal end of the delivery system.

FIGS. 33-35 illustrate an exemplary embodiment of a metering valve configuration.

FIG. 39 illustrate a representation of the fluidic performance of the exemplary valve shown in FIG. 42.

FIG. 40 is a figurative representation of the delivery system in terms of its resistive fluidic characteristics.

FIG. 41 illustrates a representation of the expected outflow rate as a function d given the resistance characteristics represented in FIG. 40 and a constant pressure supply.

FIG. 42 provides a figurative representation of a delivery system incorporating a distal fluid control configured as a shuttle valve.

FIG. 45 illustrates a distal delivery region comprising slicing hooks or simple blades which cut tissue on being advanced.

FIG. 46 illustrates an exemplary distal delivery region comprising an atherectomy blade that can be spun to facilitate the requisite tissue remodeling.

FIG. 47 illustrates an exemplary distal delivery region similar to that in FIG. 36.

DETAILED DESCRIPTION OF THE INVENTION

Figure 1:
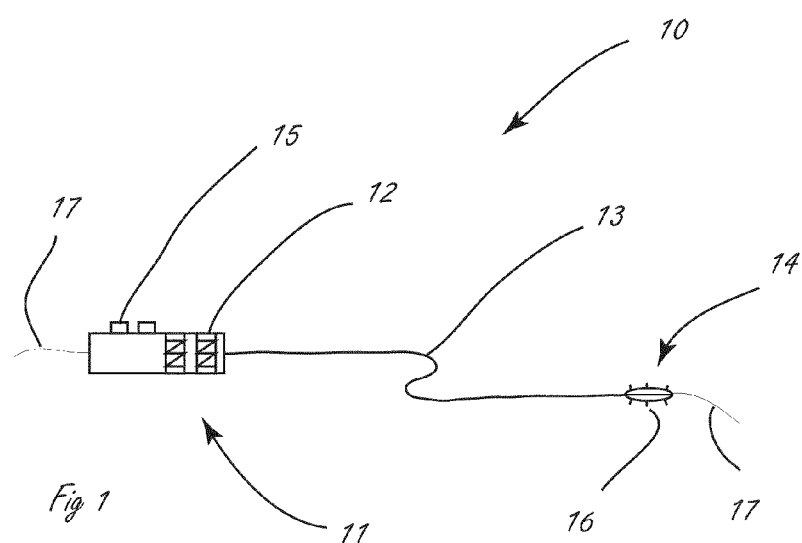
FIG. 1 illustrates an exemplary delivery system adapted to remodel tissue.

The disclosure herein relates generally to disrupting tissue and devices and systems for disrupting tissue. More specifically, the disclosure describes ways to deliver moieties to a target tissue, where the target tissue in general is not at the point of introduction, in such a way that minimal damage is produced in the tissue at the point of introduction. In some embodiments this is accomplished by jetting fluid at high velocity into the target tissue. The disclosure further describes novel agents deliverable in such systems for use in remodeling tissues. Some of these agents comprise a liquid while others do not. Additionally, although not specifically described in detail much of the disclosure may additionally be used in the delivery of therapeutic drugs.

Procedures that allow for the disruption or remodeling of tissues peripheral to body lumens, particularly while minimizing disruption to the inner surface of the body lumen and often the tissues comprising the wall of the body lumen are advantageous in a number of medical procedures. Such procedures include but are not limited to: disruption of nerves in the medial and adventitial tissue surrounding body lumens such as arteries and veins, including the renal arteries and pulmonary arteries and veins, disruption of cancerous tissues surrounding body lumens such as the esophagus for the treatment of various cancers, and urethra for treatment of various cancers such as prostate cancer. Such remodeling treatments may additionally be used to shrink tissues such as sphincters of the bowel, urethra, stomach, or intestines, amongst others. Further advantage is obtained when such procedures can be achieved percutaneously, which include endovascular, or minimally invasive delivery of the apparatus required to facilitate the procedure. Additionally, the ability to refine or continue the remodeling of the target tissue after the completion of the percutaneous or minimally invasive procedure has advantages where the outcome of the initial procedure is unclear for some period of time following the procedure or where some level of healing obviates the damage and further remodeling is required. The various configurations of the apparatus and associated methods described below facilitate such procedures.

Although the devices described herein are particularly useful for delivering agents to tissues peripheral to body lumens from within the body lumen, they also will have application in the delivery of agents via pathways and/or in locations independent of body lumens. Such uses include treatment of tumor such as those of the liver or lung.

The embodiments described herein associated with the delivery of moieties comprising fluids provide one or more of the following advantages over that which has been described: improved ways for controlling the consistency in dose and or velocity for multi jet systems across the jets; ways for controlling the dose; use of a constant pressure source while achieving metered bolus delivery while maintaining high initial fluid velocity and control of fluid velocity; and minimizing leakage of delivered material while not in delivery cycle. Additionally, in some embodiments the delivery of the fluid jets is controlled in a distal region of the delivery system, thereby minimizing negative effects of system capacitance and long fluid channels on rate at which peak fluid velocity is attained at an exit aperture and delivered dosage. Additionally, damage that is caused by moving a fluid jet while it is constantly activated and slicing large areas of tissue may be minimized by minimizing the duration of on cycles.

In some embodiments mechanical disruption of the tissue is effected by high velocity fluid jets situated at or near the target site. The jets may be located at the inner surface of a body lumen and directed thru the body lumen towards the target tissue. The jets, as they enter the body lumen, are highly focused and therefore interact with a small area of the adjoining lumen wall and volume of adjoining tissue. As the jet passes through the lumen wall, the fluid interacts with the tissue and is spread over a larger volume of tissue, disrupting an increasingly larger area of tissue. However, as the area of interaction is increased the fluid's direct interaction is dissipated and so is the associated damage. The direct interaction of the fluid may be to cut, separate, or swell. In some embodiments the jet may be moved to create a slice in adjoining tissue. The jets may additionally be designed such that the shape of the injected fluid volume would be caused to spread in one or two directions normal to the forward direction as it enters the tissue.

Alternatively, in some embodiments, the source of the high velocity jets may be passed through the inner surface of the lumen wall and into the wall of the body lumen, or the source of the high velocity jets may be passed completely through the body lumen into the tissue surrounding the body wall. The apparatus may also be configured such that combinations of these approaches may be performed.

In some embodiments the fluid delivered via the high velocity injection system is an ablative media such as one of those described below. An ablative material may be delivered to the target tissue without passing any portion of the delivery structure through the wall of the body lumen. Since needles or other structures capable of fraying or tearing the body lumen are not passing through the body lumen, no motions associated with the delivery of the delivery structure or those associated with movement of the patient can cause damage to the body lumen. This may be especially important where the body lumen is frail or where a tear in the body lumen could cause uncontrollable bleeding. Additionally, the cross section of a jet will be smaller than a delivery needle of comparable lumen size.

Some moieties or agents that can necrose tissue, capable of delivery in the fashion described, are hypertonic or hypotonic solutions which induce drying or bursting of cells. In the case of hypertonic, simple salt solutions and alcohols may be used to these ends. ETOH and mixtures of ETOH and $H_2O_2$ are particularly useful as such ablative fluids. The $H_2O_2$ in this mixture brings about additional damage as a result of oxidative stress.

Another set of agents useful for necrosing tissues are those which generate heat and can be delivered in the fashion so far described. These materials, upon interaction with each other or the environment of the target tissue, generate heat as a result of an ensuing chemical reaction or solubilization. Examples of materials which when contacted with water in the target tissue begin a reaction which is exothermic include; iron particles, exothermic salts, An exemplary, but incomplete, lists of salts which can be used to this purpose are $CaCl_2$, $CaSO_4$, $MgSO_4$, $K_2CO_3$, $Na_2SO_4$. These salts when delivered as a suspension in a non-aqueous carrier, such as a light oil or alcohol amongst others, generate heat upon rehydration. When appropriate masses of salt are delivered to a small volume of tissue the heat generated from the hydration of the salt and the consumption of water in the local environment will both necrose the tissues adjacent to the delivery zone. The conformation of the salts as delivered for this purpose can further add to the heat generating capability. For example, the salts can be finely divided such that surface to volume ratio is increased and therefore the rate of rehydration and heat generation is enhanced. Finely divided salt particles can range in size from about 0.1 to about 100 microns. Especially useful for this purpose would be the suspensions of nanoparticle sized particles of the salts in which the surface to volume ratio is even further enhanced. These nanoparticles having a size range of 10 nm to 100 nm. Nanoparticles of NaCl, delivered in a light oil or reagent grade alcohol, upon delivery to a target tissue will upon solubilization create both an endothermic reaction and a hypertonic local environment. The oxidation of iron particles provides another system which will behave in a fashion similar to that just described for the exothermic salts. Any such system which relies on such reactions and incorporates a particle as part of the delivered material will behave in much the same fashion as the salts and iron particles described above and will also benefit from an increase in surface to volume ratio such as that associated with decreasing the size from micron to nano dimensions. Other examples of materials which may be mixed at the target location include acids and bases such as: HCl and NaOH, or weak acids and metals such as HCl and Mg, catalyzed polymerization reactions such as that for methyl methacrylate resins, many others can be chosen form, which are familiar to those skilled in the art. An acid or base may also be delivered independently of the other. The use of acetic acid is such an example which has a demonstrated usefulness in ablating tumors.

Yet another set of agents useful for tissue remodeling, where the target tissue are specifically nerve tissues, are nerve toxins such as the botulinun neurotoxins or capsacin. Many other irreversibly acting nerve toxins, known to those familiar with the art, may be delivered in this fashion.

In other circumstances blood or blood products may used as an agent. In this circumstance the blood may be separated and only plasma used, or alternatively the platelets and cellular material may be used. When preparations containing cells are used the preparation may be homogenized to break down the cell structures. The preparation may also be thinned with sodium citrate and or heparin or other anti clotting agents may be added. In yet other circumstances enzymes including neurolytic and necrotizing may be used. Detergents may also be used independently or in combination with any of the fluids described herein.

In some instances it may be advantages for the agent to be deliverable in a low viscosity form and then on interaction with the environment on the target tissue increases in viscosity possibly becoming a gel. An acid solution comprising collagen, on introduction to the roughly normal pH of a target tissue, will polymerize forming a resorbable gel like material which may additionally comprise nanoparticles or other materials described herein.

In some embodiments disruption or remodeling is achieved by an externally induced interaction between a material delivered to the target tissue and the target tissue. Such materials are configured to be delivered to the target site by percutaneous or minimally invasive procedures. Upon completion of material delivery, the material is induced to facilitate the remodeling by an energy field which is created at a site external to the body and directed to the target site by non-invasive means. The induced interactions may be creation or release of toxins or necrosing agents, the generation of heat, mechanical disruption or any other means which eventuates the necroses or loss in functionality of cells in the target tissue. These materials may additionally contain agents to enhance their contrast when viewed by radiographic, acoustic, or MRI means. It should be noted that these materials may also be energized from energy sources delivered minimally invasively or percutaneous to locations near the target tissue.

One set of materials which may be used for the generation of heat are induced to heat by the application of acoustic energy. Examples of such materials include ethyl vinyl acetate, silicone, urethanes and other materials known in the art.

Yet another set of materials that can be induced to generate heat are those capable of absorbing electromagnetic energy, in particular changing magnetic fields (inductive heating). Examples of such materials include ferrites and other iron bearing materials and materials containing Nickel. As an example, heating occurs when an alternating, uniformly high flux density magnetic field induces an alternating current in a lossy conductor. A gapped toroid can generate such a magnetic field. A solenoid's magnetic field can produce the required magnetic field for inductive heating of discrete particles. In addition to heating particles that have been distributed in the lumen of the body, the external magnetic field could also be used to couple energy into a catheter in place of electrical conductors. The external magnetic field could also be used to actuate or position features of the catheter in place of mechanisms (e.g., pull wires etc.)

Yet another use for a magnetic field would be the physical manipulation of a magnetic dipole (or multitude thereof). One use of such a manipulation would be to move a magnetic particle to a desired location in order to deliver a payload. Another use of such a manipulation would be to move a magnetic particle in such a fashion to be disruptive to the surrounding tissue. A means for inducing said magnetic manipulation could be through the use of a 3 dimensional (3D) array of solenoids whose magnetic fields intersect and form a magnetic field vector that manipulates a magnetic particle(s).

In another class of materials the necrosing agent is designed to be released or to convert as a function of energy absorption.

The fluid delivery means described herein may be used for the delivery of therapeutic agents in addition to ablative agents. One such therapeutic agent is Taxol, which may be used to minimize post treatment stenosis. Hypertensive drugs may also be delivered in this fashion.

Any of these materials can be configured for delivery by the mechanisms described above or by more conventional means commonly practiced today, such as the use of simple injection from a needle or system of needles delivered to the body lumen in the vicinity of the target tissue. In such systems the final spacial geometry of the delivered material may be important. Such a situation exists for example with regard to the denervation or necrosing of adventitial and medial tissue surrounding the renal artery for the treatment of hypertension. In this situation it can be advantages to deliver the material in a spiral pattern about the vessel in the adventitial tissue surrounding the vessel.

In some methods of use, an agent can be delivered to renal nerve tissue to disrupt the neural tissue to treat hypertension. The treatment of hypertension can be accomplished by modulating of neural signal transmission along the renal nerve. Modulation includes activation of neural activity, suppression of neural activity, denervation of tissue, ablation of tissue, etc. The relationship between renal nerve signal transmission and hypertension may be found in, for example, U.S. Pat. No. 6,978,174, U.S. Pat. No. 7,162,303, U.S. Pat. No. 7,617,005, U.S. Pat. No. 7,620,451, U.S. Pat. No. 7,653,438, U.S. Pat. No. 7,756,583, U.S. Pat. No. 7,853,333, and U.S. Pub. No, 2006/0041277, U.S. Pub. No. 2006/0206150, U.S. Pub. No. 2006/0212076, U.S. Pub. No. 2006/0212078, U.S. Pub. No. 2006/0265014, U.S. Pub. No. 2006/0265015, U.S. Pub. No. U.S. Pub. No. 2006/0271111, U.S. Pub. No. 2006/0276852, U.S. Pub. No. 2007/0129760, and U.S. Pub. No. 2007/0135875, the complete disclosures of which are incorporated herein by reference. The systems and methods of use herein can be used to disrupt the tissue to modulate neural transmission along a renal nerve in order to treat hypertension.

The above materials may be delivered as solutions with a wide range of viscosities or be viscous gels. The materials either ablative or otherwise so far described may contain contrast agents and or anesthetics. Additionally, materials may be designed such that on interacting with the target site the viscosity increases or the material gels, or mixed on delivery such that they the viscosity increases or the material gels at the target site. Alternatively the materials can be formed as a solid designed to be projected into the target tissue thru the body lumen wall and into the target tissue. Such a mechanism could be driven by high velocity fluids, gases, or by mechanical means such as springs.

Any of the above materials can be combined such that they possess any of the following characteristics to fit the particular application: bioresorbable, biocompatible, or designed to remain in place for extended periods of time.

Agents which may be added to enhance contrast for imaging procedures will be dependent on the particular imaging procedure. Examples of such materials which enhance MRI imaging are Gadolinium, magnetic materials especially those containing nickel, and or ferrites. Examples of those for use with acoustical procedures are silicones, metal or metal oxide particles, amongst others known in the art. Examples of such materials useful for radiological procedures are barium sulfate, tantalum powder, or the like. These examples are not exhaustive and many alternatives, familiar to those skilled in the art may be chosen.

FIG. 1 illustrates an exemplary delivery system adapted to disrupt tissue peripheral to a body lumen. Delivery system 10 includes handle 11 and elongate delivery member 13. Associated with a distal portion of elongate member 13 is distal delivery region 14. Distal delivery region 14 includes one or more fluid controls 16. Handle 11 includes at least one delivery member actuation element 12 (two shown), and at least one fluid control actuation element 15 (two shown). Delivery member actuation element 12 can be adapted to steer delivery member 13, including distal delivery region 14, to a target location within the body. Delivery member actuation element 12 can also be adapted to reconfigure distal delivery region 14 between a delivery configuration and one or more procedural configurations. Fluid control actuation element 15 is adapted to actuate fluid controls 16 to effect peripheral tissue remodeling.

Figure 2:
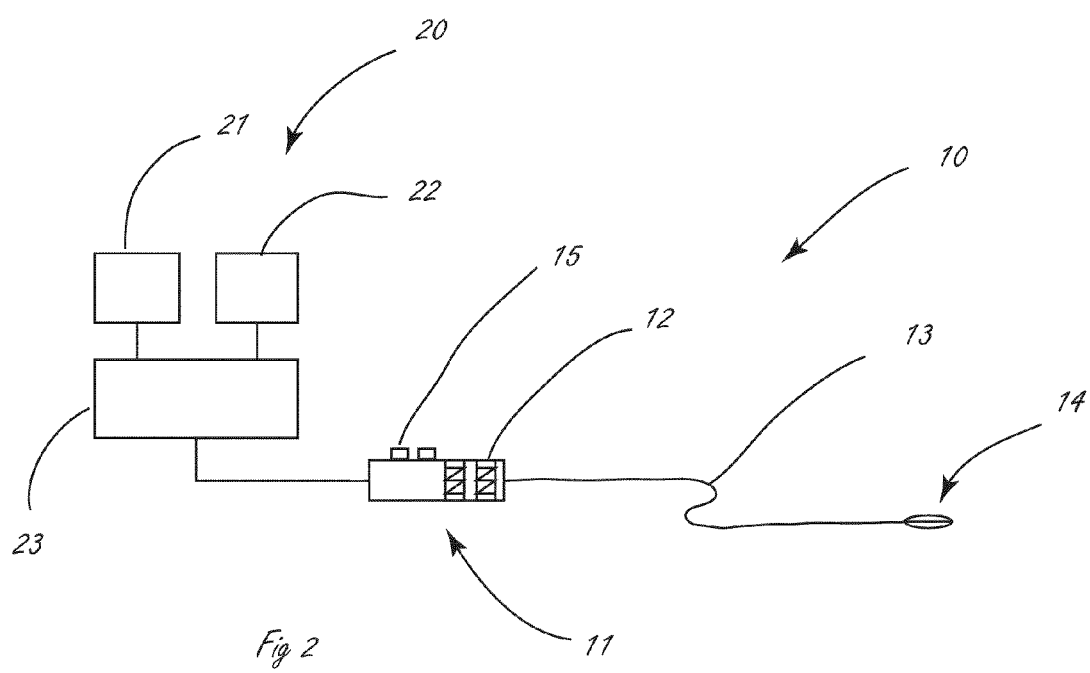
FIG. 2 illustrates an exemplary delivery system including a fluid system.

FIG. 2 illustrates an exemplary delivery system with a fluid system. Although system 20 is represented as an assembly of components separate from handle 11, fluid system 20 may be incorporated within handle 11. Fluid system 20 includes fluid reservoir 21 and optional additional reservoirs 22. Reservoir(s) interface with pressure source 23 which provides the motive force for delivering an agent to fluid controls 16 (see FIG. 1). Tissue disruption is mediated by the delivery of an agent from the fluid reservoirs to fluid controls 16. Fluid control actuation element 15 may alternatively be located within fluid system 20.

Figure 3:
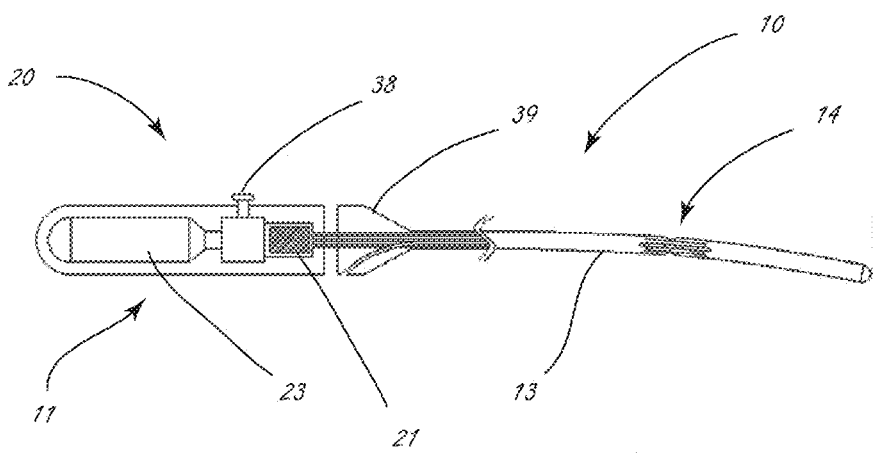
FIGS. 3-6 illustrate an exemplary embodiment of a delivery system incorporating a fluid system and a plurality of expandable tubular elements.
Figures 4, 5:
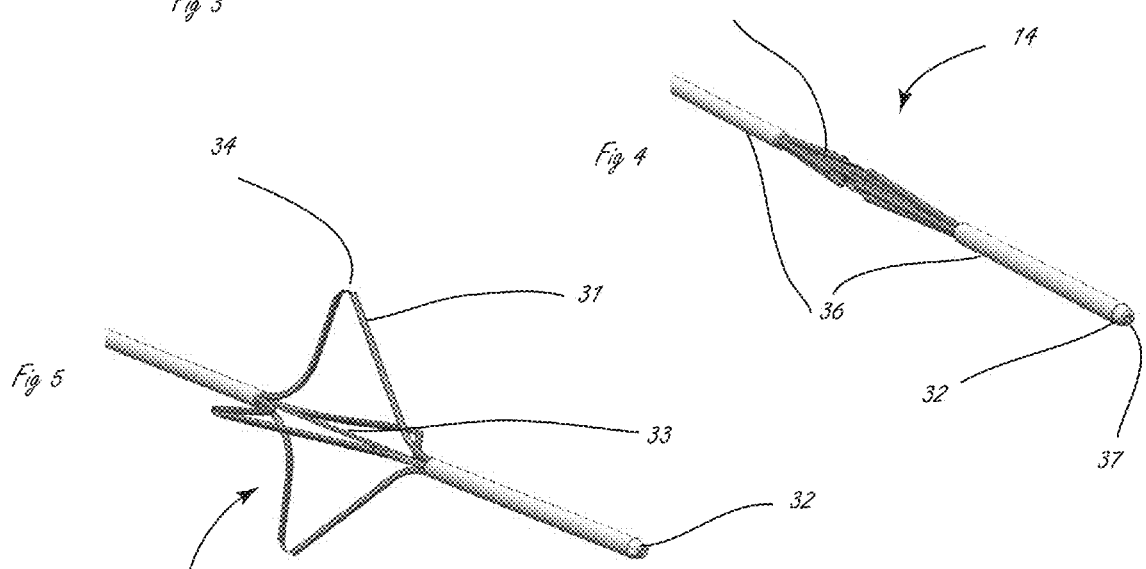
Figure 6:
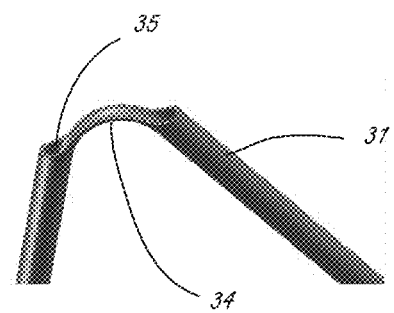

FIGS. 3-6 illustrate an exemplary embodiment of a delivery system incorporating a fluid system. Although the exemplary fluid system shown can be incorporated with any of the elongate delivery members herein, as shown in FIG. 3 the fluid system is incorporated into handle 11. Pressure source 23 includes a gas cartridge, such as a CO2 cartridge, which is in fluid communication with fluid reservoir 21, which in turn is in fluid communication with valve 38, which functions as the fluid control actuation element. In FIG. 3 delivery member actuation element 39 facilitates the reconfiguration of distal delivery region 14 from the delivery configuration shown in FIG. 4 to a procedural, or treatment, configuration shown in FIG. 5. Distal delivery region 14 comprises a plurality of expandable tubular elements 31 that are adapted to be reconfigured from respective delivery configuration as shown in FIG. 4 to expanded configurations shown in FIG. 5. In the delivery configurations the tubular elements are generally straight, and in substantial alignment with the longitudinal axis of the delivery member 13. Distal delivery region 14 is shown comprising four tubular elements 31 but any suitable number may be incorporated. Tubular elements 31 may be sealed at their distal ends, and are secured to a distal portion of outer sheath 36. Tubular elements 31 include ports 35 in fluid communication with a fluid source. In the embodiments shown, the ports are formed by removing a portion of the tube wall proximal to the distal ends of tubular elements 31. The system includes control member 33 (see FIG. 5), which is disposed within a portion of sheath 36 proximal to distal delivery region 14. Control member 33 is axially moveable with respect to the proximal portion of sheath 36 and is fixed to the sheath and tubular elements 31 distal to the distal delivery region. When control member 33 is actuated in the proximal direction, such as by actuation of delivery member actuation element 39, the distal and proximal ends of tubular elements 31 are urged closer together, causing tubular elements 31 to bend at bending regions 34 radially outward from the control member. When bent, the ports 35 are brought into contact, or at least pointed towards the lumen wall in which the distal delivery region is positioned. Fluid or agent can then be delivered from the fluid source through ports 35 to disrupt the tissue, which is described in more detail above. After the treatment has been administered, control member 33 is advanced distally with respect to the proximal portion of sheath 36 to move the ends of the tubular elements away from one another, reconfiguring the tubular elements back towards their delivery configurations. When the tubular elements are in their expanded configurations, ejection ports 35 are disposed in a plane substantially normal to that of the longitudinal axis of elongate delivery member 13. More or fewer elongate tubes can be in the distal delivery regions. Alternatively to the configuration depicted in FIGS. 3-6, the ports 35 can be staggered, which may be appropriate for different tissue disruption treatments. Flexible tubes 31 may be fabricated from any suitable flexible materials, such as nitinol. In this embodiment control member 33 has a lumen and thereby also provides the function of a guide wire lumen.

FIGS. 7-10 illustrate an exemplary method of remodeling of renal nerve plexus 43 surrounding renal artery 40 of kidney 44 using the exemplary system shown in FIGS. 3-6. Although the renal nerve plexus is depicted as two nerves for ease of representation, the renal nerve plexus actually wraps around the renal artery. Elongate delivery member 13 with distal delivery region 14 is delivered from a femoral artery or other suitable location, using known techniques, to descending aorta 41, then into renal artery 40. The delivery is facilitated by guidewire 17 which has been previously delivered by traditional means to the renal artery. Alternatively, for embodiments which incorporate steering capabilities the delivery may be facilitated without the use of a guide wire. Or in yet other alternative embodiments the delivery may be facilitated by the use of a steerable introducer catheter such as those described in U.S. patent application Ser. No. 12/823,049, filed Jun. 24, 2009, the disclosure of which is incorporated herein by reference. Upon delivery the distal delivery region 14 is expanded to a delivered configuration as shown in FIG. 8 by actuating the delivery member actuation element. In some embodiments the actuation element is advanced distally. The pressure source control element (see element 38 in FIG. 3) is activated thereby initiating the delivery of a dose configured as a high velocity jet of fluid 51 as indicated in FIG. 9. Single or multiple jets may be delivered while the distal deliver region is in any given location. The distal delivery region may be moved to a new location by releasing (or further actuating) tissue expansion control element 12 (see FIG. 3), which reconfigures the distal delivery region. The distal delivery region can then be moved to a second location, followed by actuation of the tissue interface expansion control element 12. The volume of tissue affected by the delivered fluid can be controlled by the volume of each individual fluid jet, the number of jets delivered at any given location, and the number and density of locations at which jets are delivered. After a desired number of jets are delivered to an appropriate number of locations, the action of the delivered fluid will affect a large enough volume of tissue to affect at least a portion of the renal nerve plexus, herein described as renal nerves, passing through the affected volumes of tissue and indicated in FIG. 10. Any of the systems described herein can be used in the method shown in the exemplary method of FIGS. 7-10.

Figure 11:
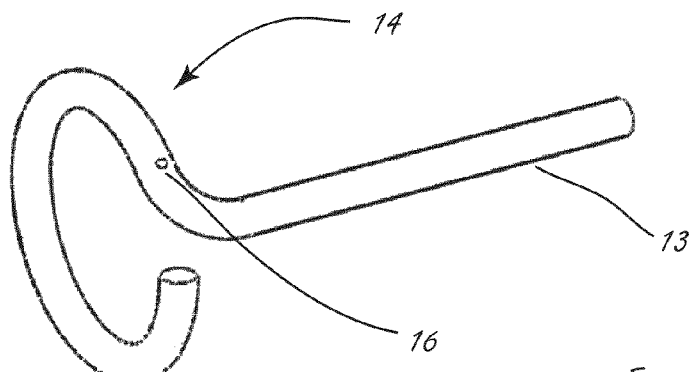
FIG. 11 illustrates an exemplary reconfigurable distal delivery region that is an extension of an elongate delivery member.

FIGS. 11-19 illustrate various distal delivery regions 14. FIG. 11 represents a reconfigurable distal delivery region which is an extension of elongate delivery member 13. In FIG. 11 the distal delivery region comprises an elongate tubular element in a treatment, or expanded, configuration. In the delivery configuration (not shown), the elongate tubular element is in a substantially straight configuration. During delivery the distal delivery region 14 substantially co-aligns with elongate delivery member 13 and upon exiting a delivery catheter assumes the configuration in FIG. 11 because of the resilient characteristics of the material. For example, the distal delivery region can be comprised of nitinol and utilize the superelastic property of nitinol to self-expand when deployed from a delivery catheter. The elongate tubular element has a generally circular or elliptical configuration such that the contact region between the tubular element and the lumen wall falls roughly in a plane and has an elliptical or circular shape. Some embodiments use devices and methods shown in co-owned pending U.S. patent application Ser. No. 12/823,049, filed Jun. 24, 2009, wherein a tensioning element and a compression element are operated in opposition to one another. The compression element incorporates a laser cut pattern which collapses into the indicated shape. In such a configuration the resultant shape and delivery system can maintain a great degree of stiffness both along the delivery axis, in torsion, and in maintaining the shape of the tubular element. In FIG. 11, distal delivery region 14 also includes fluid control 16, which includes at least one fluid jet aperture, discussed in more detail below. When distal delivery region 14 transfers from its delivery configuration to its procedural configuration, fluid control 16 is urged against the lumen wall of the target tissue. Distal delivery region 14 may be moved from position to position by allowing it to return to its delivery configuration or in some cases by moving it in its procedural configuration.

The tissue interface of FIG. 11, although shown with the looped tissue interface sitting in a plane normal to the delivery axis, may alternatively be configured such that it is in a plane upon which the delivery axis exists. Such a configuration may be comprised of a sinusoidal tissue interface incorporating one or more cycles of the sinusoid. Additionally each cycle or half cycle may fall on a different plane rotated from the previous one around the delivery axis.

Figure 12:
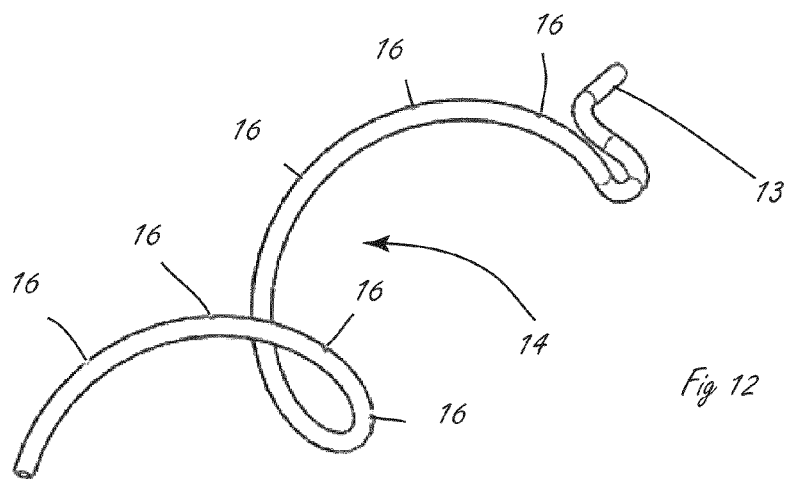
FIG. 12 illustrates a distal delivery region including an elongate tubular element that has a spiral procedural configuration.
Figure 13:
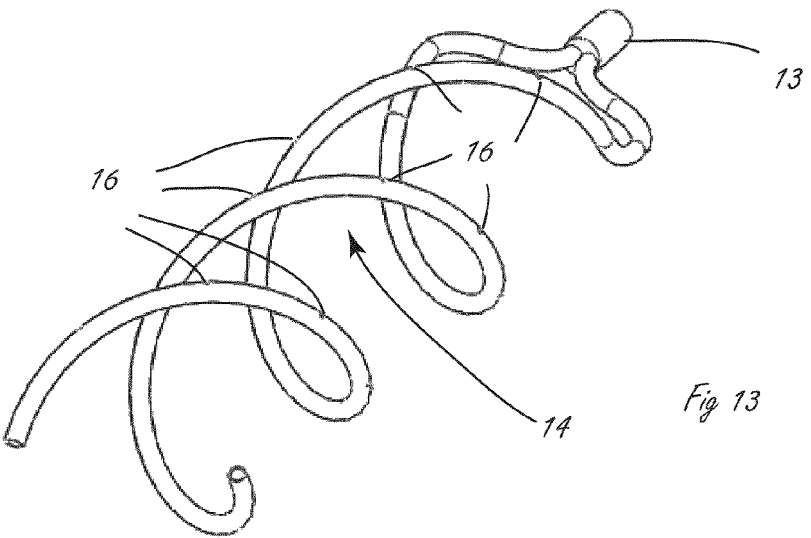
FIG. 13 illustrates a distal delivery region including first and second tubular elements that have spiral procedural configurations.

FIG. 12 illustrates a distal delivery region including an elongate tubular element that has a spiral procedural configuration (as shown), such that the contact regions between the tissue and the tubular element have a spiral configuration. The device in FIG. 12 is adapted to be actuated in similar manner to the device in 11. FIG. 13 illustrates a distal delivery region 14 including first and second tubular elements, which are adapted to be actuated in similar fashion to the device in FIG. 12. The elongate tubular elements in FIG. 13 have spiral configuration when expanded, and their contact regions with the target lumen are spiral. The elongate tubular elements shown in FIGS. 12 and 13 include a plurality of fluid controls 16. The expanded spiral structures of FIGS. 12 and 13 urge the associated remodeling elements 16 into contact with the target lumen. With a plurality of elongate elements as in FIG. 13, forces from the plurality of tubular elements against the lumen wall may create more stable contact regions between the tubular elements and the lumen wall.

FIG. 14 illustrates an exemplary portion of a distal delivery region. Distal delivery region 14 is a variation of that of FIG. 12, wherein the spiral element comprises two spring elements 18 arranged on either side of shuttle valve 50 incorporating a plurality of fluid controls 16.

FIGS. 15 and 16 illustrate perspective and end views, respectively, of an alternative embodiment of the distal delivery region. Distal delivery region 14 includes a tubular element with a general spiral treatment configuration, and includes a plurality of penetrating remodeling elements 19. Remodeling elements 19 can be used to remodel tissue in a number of different ways. Procedurally, the distal delivery region is delivered to a target lumen with penetrating remodeling elements 19 retracted with the distal delivery region in a delivery configuration. The elongate element is then reconfigured into a spiral configuration. Remodeling elements 19, which were retracted during delivery, are then advanced distally through the elongate element into the configuration as shown in FIGS. 15 and 16. The remodeling elements may then be used to remodel the target tissue by any of mechanical damage resulting from high velocity jet interactions such as cutting or swelling and/or physical interaction of a cutting or macerating element, delivering a tissue disruption agent therethrough, delivering RF energy, or any combination thereof. Penetrating remodeling elements 19 may comprise fluid controls as described below.

FIGS. 17 and 18 illustrate two variations on the distal delivery region shown in FIGS. 3-6. In both designs, the distal delivery region control element 37 (which has a guide wire lumen therethrough) is retracted proximally relative to outer sheath 36, which foreshortens the distal delivery region 14. This in turn causes tubular elements 31 to expand and engage the lumen wall. In FIG. 17, each flexible tube incorporates needle valves including apertures 52, as described herein. When tubular elements 31 are expanded, fluid apertures 52 are moved into contact with the lumen wall. In FIG. 17 a section of the outer sheath 36 has been removed to show valve control wires 64 extending through the fluid supply lines 65. The device of FIG. 18 expands in the same fashion, but comprises shuttle valves (described in more detail herein) rather than needle valves.

The exemplary alternative distal delivery region shown in FIG. 18 is shown incorporating four shuttle valves, each comprised of valve movable member 57 (see FIGS. 21 and 23), a valve stationary member 58 (see FIGS. 21 and 23), and a plurality of apertures 60. An alternate way to expand a distal delivery region is to incorporate a balloon. FIGS. 19 and 20 show two exemplary distal delivery regions incorporating shuttle valves. Both embodiments comprise a balloon which is contoured to allow blood flow when the balloon is inflated. Blood flow is maintained in a spiral fluid path adjacent to the lumen contact zone comprising the shuttle valve. In FIG. 19 fluid control 60 is a shuttle valve incorporated within the balloon 24 and in FIG. 20 fluid control 60 is a shuttle valve incorporated on the balloon. These embodiments may alternatively comprise traditional non perfusion balloons.

In some situations the delivery devices described herein may be configured such that a single fluid control actuates a plurality of apertures 60.

Figure 21:
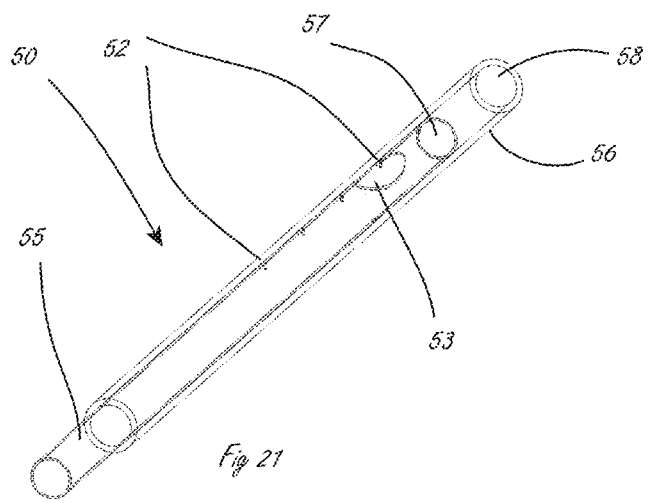
FIGS. 21-24 illustrate distal delivery regions that include incorporates one or more apertures on outer and inner tubular members.
Figure 22:
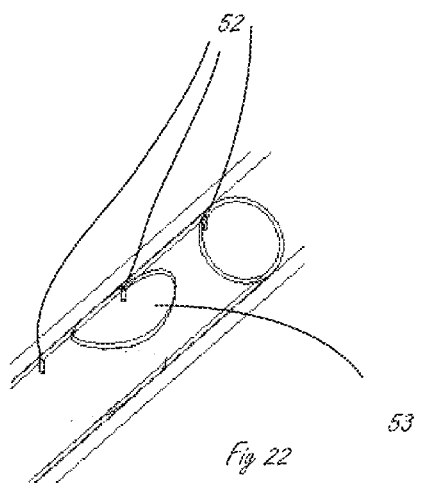

FIGS. 21-24 illustrate two variations on shuttle valves capable of being incorporated in a distal delivery region. The valve of FIGS. 21 and 22 (FIG. 22 is a close up view of a portion of the device in FIG. 21) incorporates one or more apertures 52 on outer member 56 of the valve, and an inner member 55, axially moveable with respect to outer member 56, incorporating a masking aperture 53. Apertures 52 are smaller than masking aperture 53. An individual aperture 52 is selectively addressed when the sliding inner masking aperture 53 is slid into a position adjacent aperture 52. In one configuration, members 55 and 56 are sealed at their distal ends 57 and 58 respectively. Alternatively, the member adapted to be moved with respect to the other member may be left open when the design is such that the length of tubing distal to masking aperture 53 is long enough to cover all of apertures 52 distal to the addressed aperture. Inner member 55 and outer member 56 are configured such that the outer diameter of the inner member and the inner diameter of the outer member are closely matched thereby creating an annular region of minimum cross section and high fluid resistance. Alternatively, or in addition to, the inner movable member or sections thereof may be designed such that under the loads experienced while pressurized it expands and thereby decreases the annular cross section thereby further increasing the fluid resistance.

In FIG. 21, by moving larger aperture 53 with respect to smaller apertures 52 such that aperture 53 is in alignment with a given smaller aperture, that smaller apertures 52 can be selectively addressable, increasing the amount of fluid that flows from that valve. When a given valve is addressed, the other valves are not addressed. In this embodiment the valves may be selectively addressable in series. That is, as aperture 53 is moved from a first aperture 52 to a second aperture 52, the first and second apertures are selectively addressed in series. Alternatively, when movable member 53 is allowed a rotational degree of freedom around the axis defined by its central lumen, the movable member 53 may be rotated 90 degrees and moved past smaller apertures 52 without addressing them, then rotated 90 degrees in the reverse direction when aligned with the aperture intended to be addressed.

Figure 23:
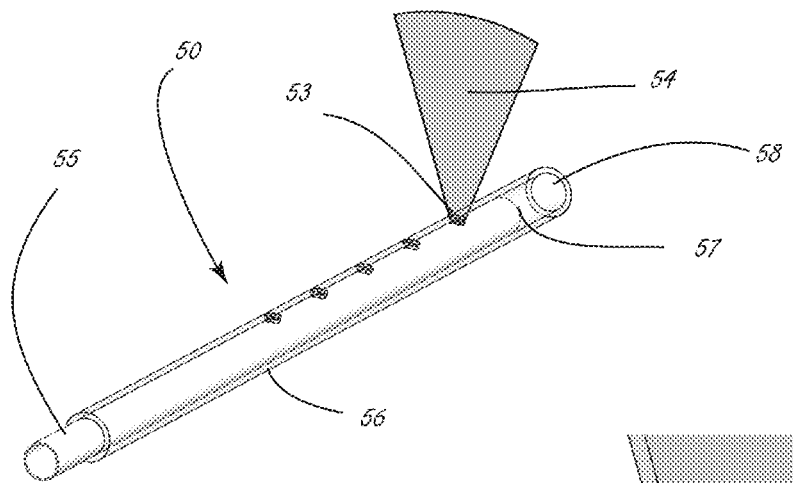
Figure 24:
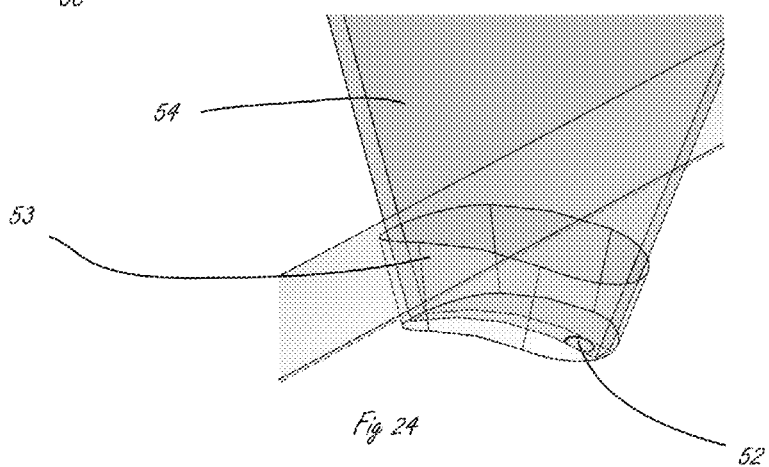

FIGS. 23 and 24 depict an alternative variation on a shuttle valve wherein masking aperture 53 is located on outer stationary member 56 and aperture 52 is located on inner movable member 55. Masking aperture 53 can be used to an additional advantage as a mask that creates a field of view 54 addressable by inner aperture 52. The aperture 52 may be rotated about the cylindrical axis of the outer stationary member 56 within the mask forming a field of view 54. The field of view 54 forms the core of the remodeled volume of damaged tissue peripheral to the lumen. The field of view 54 may alternatively describe a slice in the tissue resulting from the jet interaction with the tissue. By rotating aperture 52 out of the field of view of masking apertures not intended to be addressed, any selection of fields of view 54 defined by masks 53 may be addressed for fluid delivery.

In some embodiments, the fields of views illustrated in FIGS. 23 and 24, and in other embodiments herein, illustrate exemplary patterns in which tissue is cut or severed by the tissue remodeling therapies described herein.

The apertures 52 described herein can fall within a range of diameters, or surface areas when not circular in cross section. For delivery flows in the range of about 1 to about 20 mL/min, diameters of about 0.005 in to about 0.0005 in will be of particular value. The aperture should be sized such that the peak velocity of the outflow reaches a minimum of about 10 m/sec, with about 75 to about 150 m/sec being more optimal for greater penetration and minimizing erosion. In some situations velocities of greater than about 150 m/sec will be useful in achieving even greater penetration.

The tissue interface means described herein provide for a means of stabilizing the fluid apertures in contact with tissue in a manner that minimizes movement of the aperture relative to the adjacent tissue. The risk of dissections associated with the use of fluid jets is thereby minimized. Additionally, by incorporating of distal fluid controls, the period over which agents are delivered can be controlled. By providing jets of agent in short bursts of 1 second or less, preferably 100 msec or less, unexpected movements will result in multiple punctate wounds as opposed to a linear dissection.

Given the relatively small cross sectional areas associated with the fluid apertures in the devices described herein, it is generally advisable to filter liquid agents prior to use and/or to incorporate filters proximal to the distal fluid controls.

Figure 25:
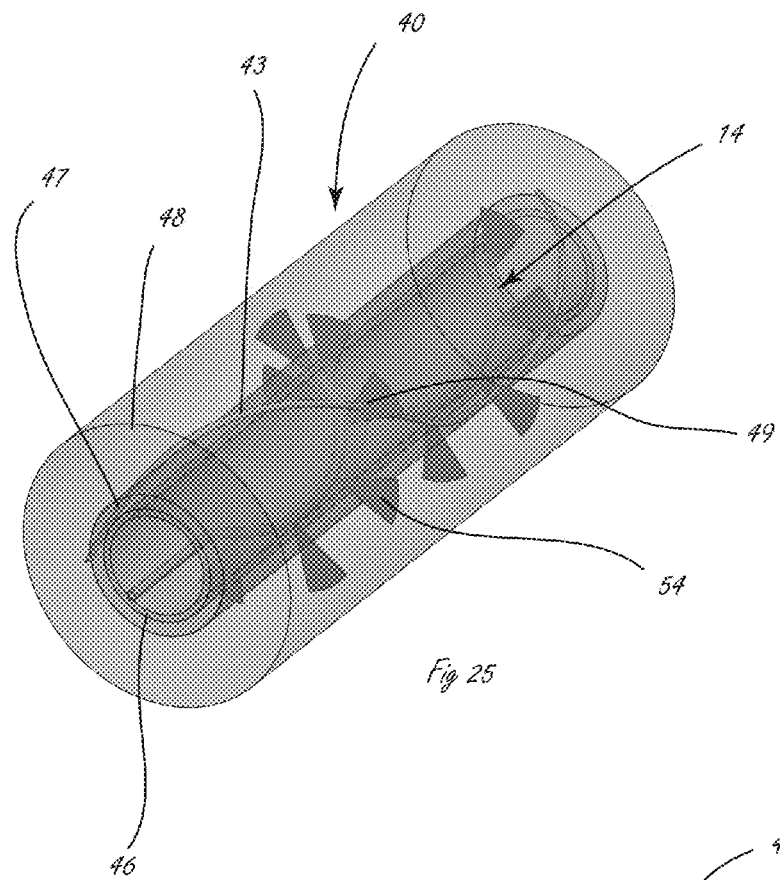
FIGS. 25 and 26 illustrate a spiraled distal delivery region expanded in a renal artery.
Figure 26:
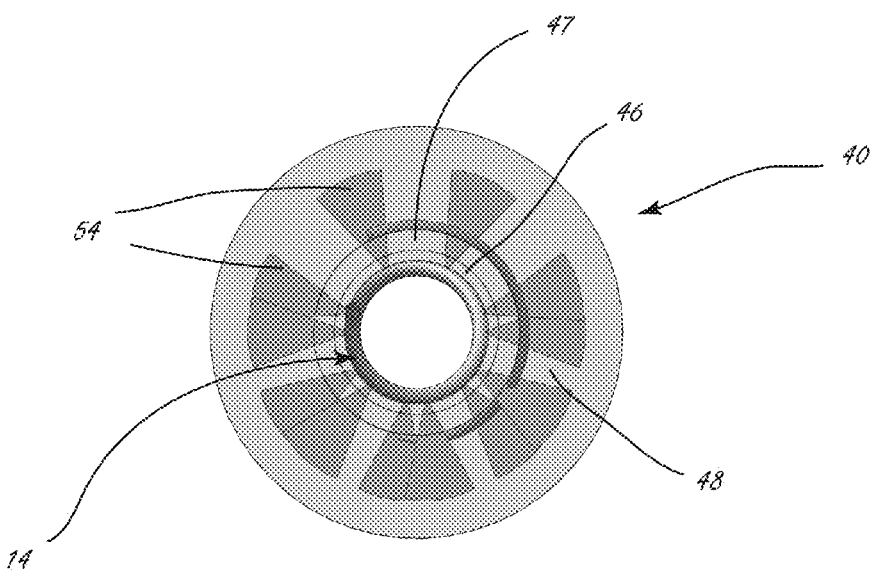

FIG. 25 illustrates the spiraled distal delivery region from FIG. 12 incorporated with a shuttle valve design from FIG. 23, and expanded in renal artery 40. The pattern of tissue damage is indicated by fields of view 54. FIG. 26 illustrates a view normal to the direction of blood flow demonstrating how the projection of such patterns normal to the axis of the lumen can produce both dense and overlapping coverage further from the lumen and spaced non-overlapping coverage closer to the lumen. The density of jetting structures and associated fields of view may be increased to a point where the remodeled zones themselves overlap. The associated density and field of view required will be dependent on the particular way in which the damage is created. Given an aperture of relatively small dimension, as illustrated in the smaller apertures described herein, the ratio of the volume of damaged tissue close to the aperture, seeded by the field of view 54, can be minimized relative to volume of damage further away. As illustrated, where the lumen is that of a renal artery, this means minimizing damage to endothelium, tunica intima 46, the tunica media, and tunica adventitia 47, with extensive damage to adventitia 48. When desired, the aperture's field of view 54 may be increased to correspondingly increase the damage at the tunica media 47. As indicated above any of the fields of view indicated may be addressed in any sequence by appropriately controlling the movable member of shuttle valve 23. In this way more or less of the renal nerve may be disrupted.

The devices of FIGS. 21 and 23 may be configured such that only a single fluid control may be addressed at one time or such that multiple fluid controls may be addressed at one time.

FIGS. 27-32 illustrate various configurations and aspects of exemplary needle valves that can be activated from the proximal end of the delivery system, allow for minimal leakage in a closed configuration or high fluid resistance when not activated, allow minimal fluid resistance in an open configuration, provide the ability to provide a metered dose from the valve, and are capable of both serial or parallel activation. All valves are activated by a valve control member 64, which is adapted to be axially moved (forward and back) within fluid supply section 65, both of which terminate in a handle (not shown). In some instances there is also a metering or delivery section 66. In FIGS. 27-29, the needle valve is supplied by a pressurized fluid source maintained at relatively constant pressure which is in fluid communication with the aperture 52 via supply section 65, within which is valve control element 64. In any cross section within which valve control member 64 is contained within the fluid supply section, there is a relatively non-restrictive fluid flow cross section, shown in FIG. 27 as annular region 63. Distal to the fluid supply section is delivery valve section 66, which in the embodiment of FIGS. 27-29 is of smaller diameter than the supply section. In association with the valve section is needle element 61 which is disposed within delivery section 66. The clearance between the needle and delivery section lumen is small, such that it forms a narrow restrictive annular region of relatively high fluid resistance 62 as compared to that of the lumen with the needle removed. Additionally, the fluid flow cross section of supply section 62 is much smaller than 63. For instance, for a particular concentration of ETOH and water, a restrictive fluid flow cross section created by a 0.5 inch long 0.004 inch inner diameter needle in a 0.005 inch inner diameter tube will have a fluid resistance of 450 psi/mL/min. The corresponding resistance for the same tube without the needle will be approximately 5 psi/mL/min. In comparison, a supply section created by a 32 inch long tube with a 0.015 inch outer diameter and a 0.010 inch outer diameter control wire will have a corresponding fluid resistance of approximately 1 psi/mL/min. In this example the fluid resistance of the system in the open configuration is approximately 75 times less than that of the closed system, and in a constant pressure environment would leak at a rate of about 1/75 the open rate in the closed configuration. In the configurations represented in FIGS. 27 and 28, an aperture 52 is created on the side of delivery section 66 near the sealed distal end. In the configuration represented in FIG. 29, the aperture is the open distal end of the delivery section.

A variation on the example of FIGS. 27-29 is represented in FIGS. 30-32. FIG. 30 shows a needle valve in an open configuration where the end of the needle is maintained just within the lumen of the delivery section 66. In FIG. 31, the valve is partially closed with a section of a restrictive fluid flow cross section 62 indicated. FIG. 32 shows the valve fully closed with the distal face of the guide 69 seated against the proximal face of the end seal of the supply section 65. If required, further increases in fluid resistance can be attained in the fully closed position by incorporating an elastomeric guide 69 or an elastomeric distal face to guide 69 which would seal against the proximal face of the end seal on the supply section 65. Guide 69 additionally incorporates relieved areas to create a large fluid flow cross section 63.

FIGS. 33-35 illustrate an exemplary embodiment of a metering valve configuration. Guide 69 is configured such that it forms a narrow restrictive annular aperture with the end of the delivery section 66, which in this configuration may be the end of the supply section 65. When the valve control member 64 is actuated proximally, fluid leaks across the restrictive fluid flow cross section 62, filling the distal metered volume 67. At this point the fluid resistance between the supply side and the delivery side is the sum of that associated with the exit aperture 52 and the restrictive cross section 62. When the valve control member 64 is released the resistance associated with fluid flow across cross section 62 goes to zero and the guide moves as a plug of delivery fluid. The movement of the guide imparts minimal additional fluid resistance to the system, thereby allowing the pressure across aperture 52 to attain levels comparable to those seen with no guide in place. This state remains in effect until the guide runs into the distal sealed end 68 of the delivery section 66, as shown in FIG. 35. At this point the outflow resistance becomes that associated with the restrictive fluid flow cross section 62 and aperture 52 again. In this way, the delivered volume—that volume delivered under high pressure and at high velocity which penetrates the intima—is that which was disposed distal to the guide plug prior to its release. The delivered volume can therefore be regulated and controlled, and can be adjustable. If required, the rate at which the guide is withdrawn during the fill cycle can be matched to that of the expected fluid flow across restrictive fluid flow cross section 62 such that there is minimal negative pressure generated across the guide 69. This configuration behaves differently than other control elements in that the fluid resistance across the control element remains constant but the position of the control element is allowed to change. As illustrated the travel of the guide 69 is defined by the amount of proximal displacement of the guide from the distal end seal 68 which acts as its stop. In an alternate embodiment, not shown, the displacement of the guide 69 may be controlled by alternate mechanisms and the guides displacement may terminate proximal to the end seal 68.

Figure 36:
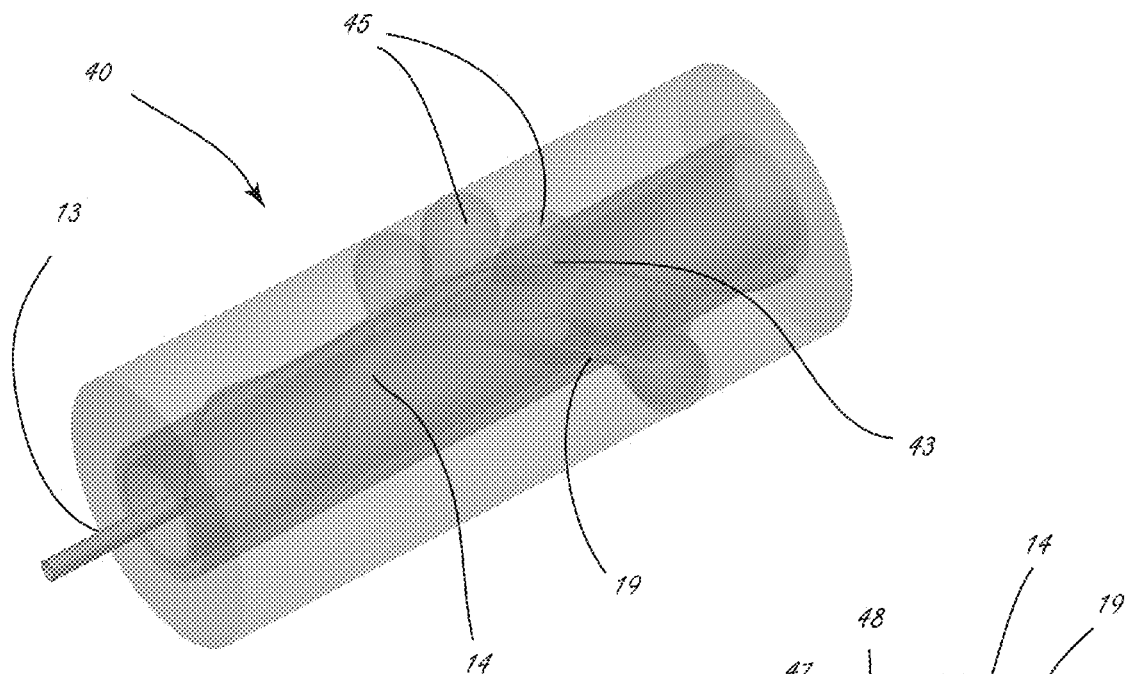
FIGS. 36 and 37 illustrate a distal delivery region including penetrating remodeling agents deployed within a section of a renal artery.
Figure 37:
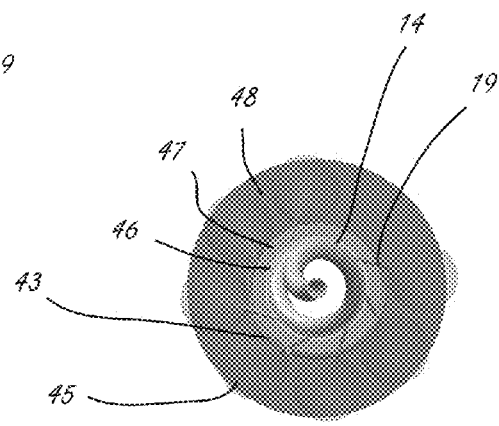

FIGS. 36 and 37 illustrate the distal delivery region of FIGS. 15 and 16 deployed within a section of renal artery 40. In FIG. 36 the end of elongate delivery member 13 just distal to distal delivery region 14 can be seen centered in the vessel. Penetrating remodeling elements 19 have been deployed from their non-deployed configuration within the distal delivery region to their deployed state, penetrating through intimal 46 and medial layer 47 of the vessel and terminating in the adventitial layer 48. Volumes of remodeled tissue 45 spiral through the adventitia, with one intersecting nerve 43. FIG. 37 depicts a view normal to the axis of blood flow for the vessel in which can be seen that the primary volume of remodeled tissue occurs beyond the intimal and adventitial layers.

Figure 38:
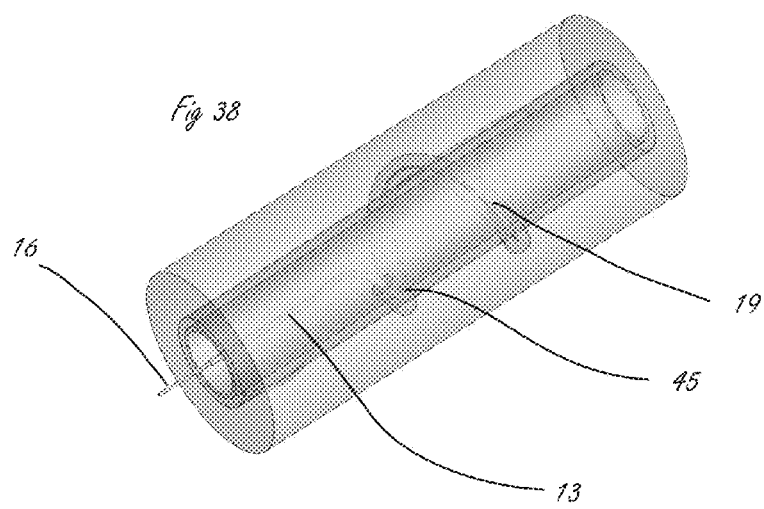
FIG. 38 illustrates an exemplary distal delivery region incorporating a remodeling element that is a needle with a helical configuration.

In yet another embodiment as depicted in FIG. 38, a penetrating remodeling element 19 is a needle. The needle has a helical configuration and delivered while contained with an outer sheath of a delivery section 13 of a delivery system, not shown. In this configuration, the outer sheath of the delivery section has a stiffness sufficient to maintain the spring element in a straightened configuration. On delivery the remodeling element is pushed distally out of the distal end of the outer sheath of the delivery system until the distal end of the remodeling element has passed into the vessel wall. The remodeling element is then twisted, which in combination with the pre-set spiral configuration allows the remodeling element 16 to screw its way around the vessel within the adventitial layer. The remodeling element can be comprised of a number of different configurations. In many of these configurations it is a conductor that may be powered with RF to deliver energy sufficient to ablate the surrounding tissue. Alternatively, it may be powered in such a way as to electroporate the surrounding tissue. The remodeling element may additionally be porous such that an ablating agent (described herein) may be delivered through the porous structure. It may alternatively be coated with an ablative agent. In those embodiments where it is used to deliver an ablative agent on or through its walls and it is conductive the electroporative capability may be used to enhance the action of the ablative compound delivered. When the remodeling element is comprised of a needle, it may also be used to leave an ablative element in the tract of its path as the element is removed by a procedure in reverse of that by which it was delivered. The material left may alternatively be one designed to absorb energy provided by an external source such as a gel containing a ferrite as mentioned elsewhere in this application.

In any of the configurations relying on the delivery of a fluid agent at high velocity, the pressure may be adjusted between delivery cycles. In this manner the volume and spatial characteristics of the remodeled tissue volume may be adjusted. Of particular value in such a situation is the incorporation of a contrast agent within the delivered media which will provide visual feedback on the remodeled volume via the particular imaging means. Such imaging means include but are not limited to CT, MRI, and ultrasound.

FIG. 42 provides a figurative representation of a delivery system incorporating a distal fluid control configured as a shuttle valve, while a representation of its fluidic performance is illustrated in FIG. 39. The system comprises a fluid and pressure source 20, which feeds a delivery system 10, as generally described above. The delivery system is comprised of elongate delivery member 13 comprising a fluid supply section feeding into distal delivery region 14, which comprises a fluid control terminating in aperture 52 from which a jet of fluid 51 is ejected under appropriate conditions of alignment. FIG. 40 is a figurative representation of the delivery system in terms of its resistive fluidic characteristics. The elements are the fluid resistance of the fluid source 83 contained within elongate delivery member 13, the fluid resistance of the fluid path within the tissue interface portion 84, and the fluid resistance of control port 80. Each of these elements has an associated capacitance which is not shown in this representation. The control port behaves as a variable resistance which is the primary characteristic under control. FIGS. 40 and 41 illustrate various aspects of the resistive fluidic performance of these components. FIG. 40 represents the resistance associated with the fluid control port 80, as a function of the displacement "d" of its control element position, and the resistances for the supply section and tissue interface portions of the system 83 and 84 respectively, which are not directly controllable in this configuration and are essentially fixed. Key positions for the jet aperture 52 relative to the masking aperture 53 are indicated on the displacement axis d as "0", "a", and "b". The point "0" corresponds to the position where the proximal edge of the jet exit aperture aligns with the proximal edge of the jet masking aperture. The position "a" corresponds to the point at which the distal edge of the jet aperture aligns with the distal edge of the masking aperture, and b represents a point where the proximal edge of the jet exit aperture is distal to the distal edge of the jet masking aperture by some distance a-b. As seen in the illustration, the fluid resistance versus displacement characteristics of the shuttle valve fluid control 80 has two distinct performance features. A constant resistance 82 is demonstrated initially which is equal to that associated with the cross section of the jet exit aperture. A second increasing resistance 81 is demonstrated when the jet aperture passes out of the masking aperture. This resistance increases as the distance d increases. FIG. 41 illustrates a representation of the expected outflow rate 90 as a function d given the resistance characteristics represented in FIG. 40 and a constant pressure supply. Outflow rate 90 is comprised of a high constant rate of outflow 91 for displacements "0" to "a" and a decreasing rate of outflow 92 for displacements "a" to "b". The regions represented by displacements "0" to "a" correspond to the on state and the displacement "b" correspond to the off state. The system resistance will be the sum of the component resistances. The scales indicated should be understood as arbitrary and the magnitude of the difference in flow and resistance in the off state versus the on state may be a few times to multiple orders of magnitude.

Figure 43:
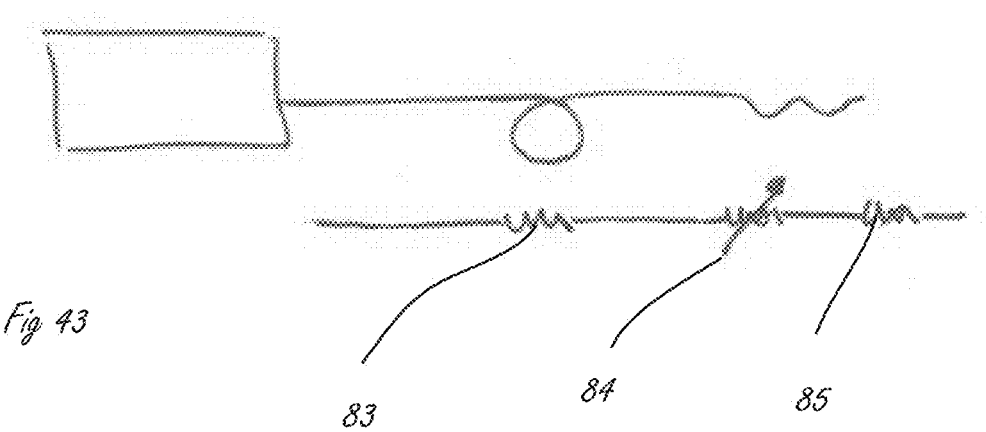
FIG. 43 illustrates the system of FIG. 39, wherein the shuttle valve is replaced by a needle valve.

FIG. 43 shows the system of FIG. 39 wherein the shuttle valve is replaced by a needle valve. This system demonstrates fluidic behavior similarly to that described for the shuttle valve variation. However certain differences associated with actuation and fabrication are notable and delineated below. In a system incorporating multiple individually and selectively addressable fluid controls, the shuttle valve based system may be configured such that control elements are comprised of two parts as is illustrated in FIGS. 21-24 above. The needle valve and metered valve variations by contrast require a separate control element and associated controllable member for each valve separately addressable. In the needle valve variation the variable resistance associated with the control element 80 is shifted to the position of the tissue interface 84, the resistance of the tissue interface and the jet exit apertures in the most distal position. Such an arrangement does not lend itself to a serial arrangement as the multiple valves require a common source which is proximal to the control element.

Given the small size of many of the critical features associated with the above described fluid controls and the extreme sensitivity of the performance of the fluid controls to the dimensions of these features, the ability to serially and or individually address each fluid control has particular value where uniformity of delivery is required. For instance, an individual device may be calibrated in such a fashion that the outflow resistance for each outflow is known and used to adjust the either or both the static source pressure or the on time such that each outflow behaves similarly with reference to the fluid delivery during an injection cycle. In addition, as noted above, the fluid media delivered may contain a contrast agent and the operator can use the visual information to change the source pressure to vary depth of penetration, duration of injection to adjust volume delivered, or provide multiple injection cycles at a given location to adjust volume of targeted tissue. The delivery cycle may additionally be spread out over time such that an initial volume is injected at an initial time, then an additional volume is injected at a later time where enough time is allowed such that information on the rate of diffusion of the delivered fluid is gained and additional volumes may then be delivered in a fashion wherein the a concentration of ablatant sufficient to ablate is maintained in the remodeled target volume for a sufficient time to remodel the tissue.

Figure 44:
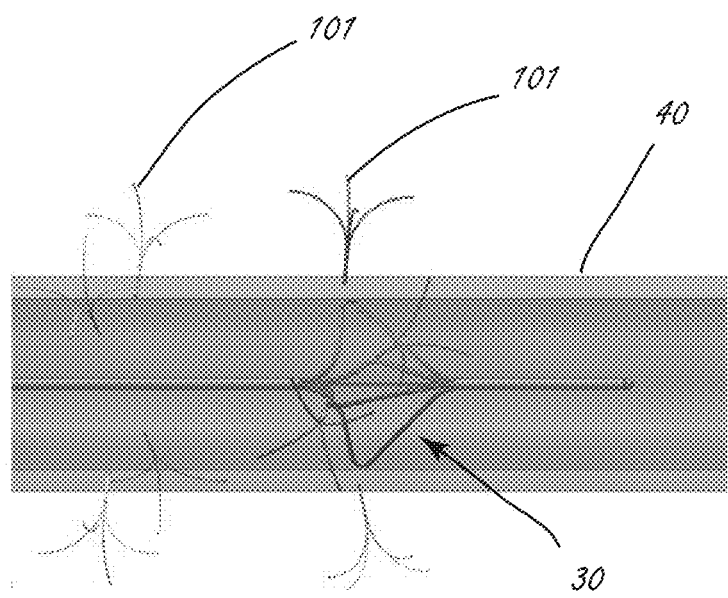
FIG. 44 illustrates an exemplary distal delivery region wherein a fluid or gas may be used to eject a component capable of external excitation or alternatively a component which upon ejection springs into a shape different than its delivery shape and in so doing damages tissue in its vicinity, thereby causing tissue remodeling.

FIG. 44 represents yet another alternative for effecting tissue remodeling where a fluid, gas, or mechanical rod may be used to eject a component capable of external excitation as described herein or alternatively a component which upon ejection springs into a shape different than its delivery shape and in so doing damages tissue in its vicinity, thereby causing tissue remodeling. In FIG. 44 spring elements 101 are shown after ejection from distal delivery region 30 through the wall of renal artery 40. As shown, multiple spring elements 101 have been ejected from two separate positions of distal delivery region 30. Spring elements 101 may be configured such that the tines are held together for a period of time past the ejection cycle. For instance they may be held together by a water soluble binder and injected in a gas, oil, or alcohol carrier. In this fashion, on residing within the tissue for a period of time the binder will be solubalized and the tines released. The release of the tines may be used to cut or macerate the tissue surrounding the tines.

It has been demonstrated in the literature that the volume of tissue affected by a needleless injection will be dependent on the spatial velocity and temporal velocity profiles of the injectate at the time of delivery. In particular, delivering a volume of fluid into a tissue mass at high initial velocity minimizes tissue damage at the entry point while allowing fluid to penetrate deep into the tissue. Maintaining the outflow at a lower velocity after the initial penetration facilitates an increase in volume delivered through the initial wound. In the above described fluid delivery systems, the control mechanism has been incorporated at the distal region of the delivery system. This allows the delivery system to be maintained at delivery pressures and thereby minimizes the filtering effects of the long narrow delivery lumens and system capacitance on the velocity profile of ejected fluid at the exit aperture.

In another alternative embodiment of a tissue remodeling device cutting or macerating devices may be delivered through or in the manner that needles 16 in FIGS. 36 and 37 are delivered. Such devices may be configured as slicing hooks or simple blades which cut on being pushed as represented in FIG. 45. Additionally such devices may be spun as an atherectomy blade to facilitate the requisite remodeling as depicted in FIG. 46 through which the rotatable cutting device of FIG. 45 is delivered. FIG. 47 shows a device as in FIG. 36. While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method of controlling the delivery of fluid from a medical delivery device, comprising:
   a medical device comprising a distal delivery region comprising a plurality of fluid controls, each of the plurality of fluid controls comprising an aperture in direct fluid communication with a region external to the medical device, wherein each of the apertures is adapted to be in fluid communication with a single fluid delivery lumen and single fluid reservoir;
   selectively regulating the flow of a fluid through the plurality of fluid controls, wherein selectively regulating the flow comprises flowing the fluid out of a first fluid control to the region external to the medical device at a high velocity and flowing the fluid out of a second fluid control to the region outside of the medical device at a low velocity, and wherein selectively regulating further comprises increasing the flow of fluid from the first fluid control while at the same time not changing the flow of fluid through the second fluid control;
   wherein selectively regulating further comprises moving the first fluid control from a closed configuration to an open configuration causing the fluid to flow from the first control at the high velocity, while the fluid flows out of the second fluid control at the low velocity; and
   wherein moving the first control to the open configuration comprises moving a first valve element with a first aperture therein relative to a second valve element with a second aperture therein until the apertures are in alignment, wherein the first and second valve elements are disposed in the distal delivery region.

2. The method of claim 1 wherein selectively regulating further comprises increasing the fluid flow from the first fluid control a first amount and increasing the flow of fluid from the second fluid control a second amount, wherein the first amount is different than the second amount.

3. The method of claim 1 wherein flowing the fluid out of a first fluid control at a high velocity comprises flowing the fluid out of a first fluid control at a velocity of at least 10 m/sec.

4. The method of claim 3 wherein flowing the fluid out of a first fluid control at a high velocity comprises flowing the fluid out of a first fluid control at a velocity between 75 m/sec and 150 m/sec.

* * * * *